US009128584B2

(12) United States Patent
Case et al.

(10) Patent No.: US 9,128,584 B2
(45) Date of Patent: Sep. 8, 2015

(54) MULTI ENERGY X-RAY MICROSCOPE DATA ACQUISITION AND IMAGE RECONSTRUCTION SYSTEM AND METHOD

(71) Applicant: Carl Zeiss X-ray Microscopy, Inc., Pleasanton, CA (US)

(72) Inventors: Thomas A. Case, Walnut Creek, CA (US); Susan Candell, Lafayette, CA (US); Srivatsan Seshadri, San Ramon, CA (US); Paul McGuinness, San Francisco, CA (US)

(73) Assignee: Carl Zeiss X-ray Microscopy, Inc., Pleasanton, CA (US)

( * ) Notice: Subject to any disclaimer, the term of this patent is extended or adjusted under 35 U.S.C. 154(b) by 215 days.

(21) Appl. No.: 13/768,689

(22) Filed: Feb. 15, 2013

(65) Prior Publication Data

US 2014/0233692 A1    Aug. 21, 2014

(51) Int. Cl.
*G01N 23/087*    (2006.01)
*A61B 6/03*    (2006.01)
(Continued)

(52) U.S. Cl.
CPC .............. *G06F 3/0481* (2013.01); *A61B 6/482* (2013.01); *G01N 23/046* (2013.01);
(Continued)

(58) Field of Classification Search
CPC ............ A61B 6/03; A61B 6/482; A61B 6/52; G01N 23/046; G06K 9/6212; G06T 11/006; G06T 15/08; G06T 5/40; G06T 5/50
USPC ............. 378/4–20, 53, 62, 96, 98, 98.2, 98.5, 378/98.9, 98.11, 98.12, 110, 112, 114–116, 378/124, 134, 156–158, 164, 204, 205, 210, 378/901; 382/128, 131, 168, 172, 276, 278, 382/284, 285, 294–300, 307, 308, 325
See application file for complete search history.

(56) References Cited

U.S. PATENT DOCUMENTS 6,418,189 B1    7/2002  Schafer
2004/0076260 A1 *  4/2004  Charles, Jr. et al. .......... 378/124
(Continued)

FOREIGN PATENT DOCUMENTS

EP    2437050 A1 *  4/2012  ............... A61B 6/03

OTHER PUBLICATIONS

Depypere, M. et al., An iterative dual energy CT reconstruction method for a K-edge contrast material, SPIE Medical Imaging, International Society for Optics and Photonics, Mar. 2011, 7 pages.
(Continued)

*Primary Examiner* — Anastasia Midkiff
(74) *Attorney, Agent, or Firm* — Houston & Associates, LLP

(57) ABSTRACT

A multi energy, such as dual-energy ("DE"), x-ray imaging system data acquisition and image reconstruction system and method enables optimizing the image contrast of a sample. Using the DE x-ray imaging system and its associated user interface applications, an operator performs a low energy ("LE") and high energy ("HE") x-ray scan of the same volume of interest of the sample. The system creates a low-energy reconstructed tomographic volume data set from the set of low-energy projections and a high-energy tomographic volume data set from the set of high-energy projections. This enables the operator to control the image contrast of selected slices, and apply the information associated with optimizing the contrast of the selected slice to all slices in the low-energy and high-energy tomographic data sets. This creates a combined volume data set from the LE and HE volume data sets with optimized image contrast throughout.

51 Claims, 15 Drawing Sheets

(51) Int. Cl.
    G06T 5/40        (2006.01)
    G06T 5/50        (2006.01)
    G06F 3/0481      (2013.01)
    G01N 23/04       (2006.01)
    A61B 6/00        (2006.01)
    G06K 9/62        (2006.01)
    G06T 11/00       (2006.01)
    G21K 7/00        (2006.01)
    G06T 15/08       (2011.01)

(52) U.S. Cl.
    CPC ............ G06K 9/6212 (2013.01); G06T 5/40
        (2013.01); G06T 5/50 (2013.01); G06T 11/006
        (2013.01); G21K 7/00 (2013.01); *A61B 6/03*
        (2013.01); *A61B 6/52* (2013.01); *G01N
        2223/419* (2013.01); *G01N 2223/423* (2013.01);
        *G06T 15/08* (2013.01)

(56)                References Cited

U.S. PATENT DOCUMENTS

2004/0264626  A1*  12/2004  Besson ......................... 378/4
2007/0280417  A1   12/2007  Kang et al.
2008/0260092  A1*  10/2008  Imai et al. ..................... 378/5

OTHER PUBLICATIONS

Cesareo, R. et al. "Material analysis with a multiple X-ray tomography scanner using transmitted and scattered radiation," Nuclear Instruments and Methods in Physics Research, Section A, 525 (2004): pp. 336-341.

Cesareo, Roberto. "Principles and Applications of Differential Tomography," Nuclear Instruments and Methods in Physics Research, Section A, 270 (1988): pp. 572-577.

Wang, Jun et al. "Automated markerless full field hard x-ray microscopic tomography at sub-50 nm 3-dimension spatial resolution," Applied Physics Letters 100, 143107 (2012).

International Search Report and Written Opinion of the International Searching Authority, mailed on Oct. 20, 2014, from counterpart International Application No. PCT/US2014/011689, filed on Jan. 15, 2014.

Norbert J. Pelc Sc.D., "Dual Energy CT: Physics Principles," slide show presentation, Departments of Radiology and Bioengineering, Stanford University, 2008, 11 pages.

* cited by examiner

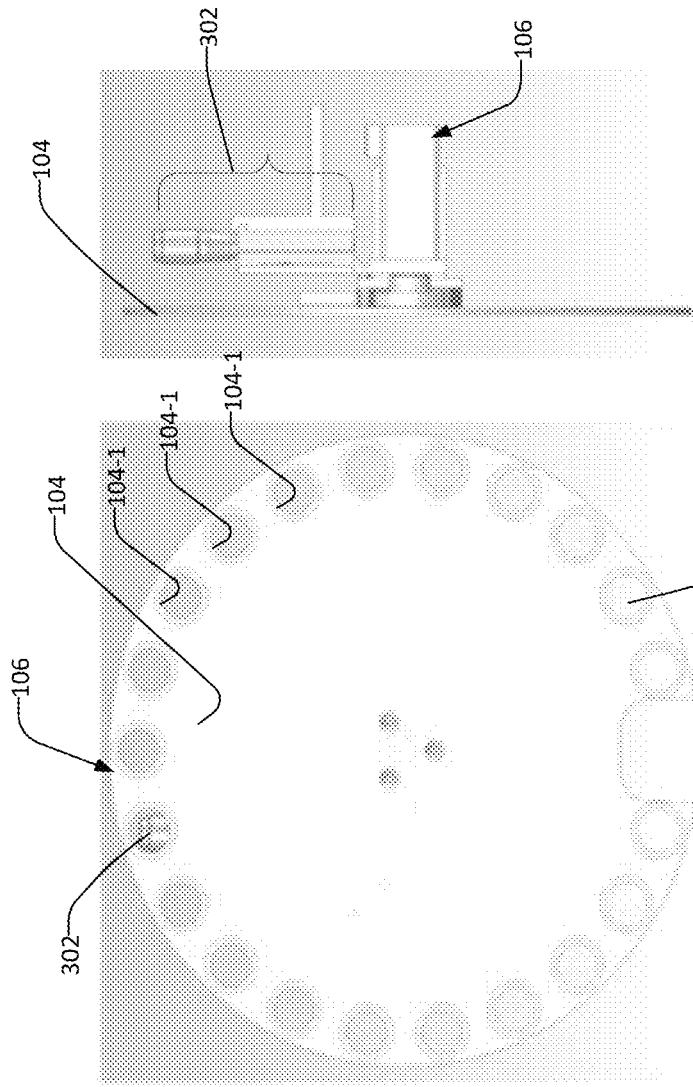
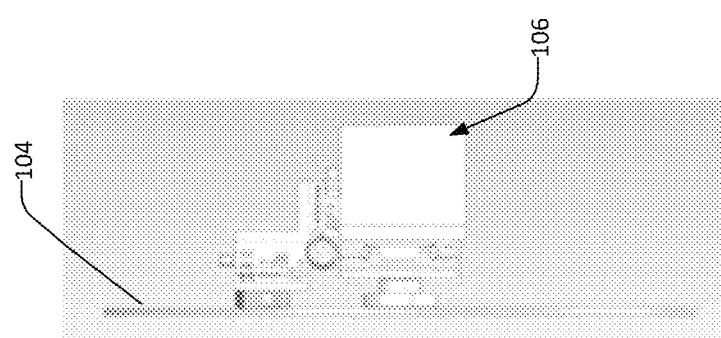

MULTI ENERGY X-RAY MICROSCOPE DATA ACQUISITION AND IMAGE RECONSTRUCTION SYSTEM AND METHOD

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

High resolution x-ray imaging systems, also known as X-ray imaging microscopes ("XRM"), provide high-resolution/high magnification, non-destructive imaging of internal structures in samples for a variety of industrial and research applications, such as materials science, clinical research, and failure analysis to list a few examples. XRMs provide the ability to visualize features in samples without the need to cut and slice the samples. XRMs are part of the field of x-ray microscopy.

XRMs are often used to perform computed tomography ("CT") scans of samples. CT scanning is the process of generating three dimensional tomographic volumes of the samples from a series of projections at different angles. XRMs often present these tomographic volumes in two-dimensional, cross-sectional images or "slices" of the three dimensional tomographic volume data set. The tomographic volumes are generated from the projection data using software reconstruction algorithms based on back-projection and other image processing techniques to reveal and analyze features within the samples.

Operators select scanning parameters, such as x-ray energy value, exposure time, and filter settings, and direct the XRM to perform a CT scanning "run." For each run, the operator or an automatic loader installs the sample between an x-ray source and an x-ray detector system, and exposes the sample to a beam of x-rays. The XRM rotates the sample in the x-ray beam, and its detector system detects the x-rays that are transmitted through and modulated by the sample at each rotation angle.

During a run, the sample absorbs or scatters some of the x-rays before passing through to the x-ray detector system. The x-ray detector system receives the attenuated photon flux of x-rays that pass through and are spatially modulated by the sample. The detector system creates an image representation, in pixels, of the x-ray photons that react with the detector system. X-ray absorption increases with sample density and thickness, and is also generally higher for elements within the sample that have a higher atomic number ("Z") in the periodic table.

Operators use standard operating procedures and best known methods ("BKM") for the selection of the optimum "run" conditions. BKMs are written instructions for workflows that are written instructions for workflows that help the operator determine the optimum x-ray source voltage settings, beam pre-filter and detector settings associated with a particular sample. The resulting three-dimensional image representation of the sample after processing is also known as a reconstructed tomographic volume data set.

Operators typically operate an XRM using software control. For each scanning run, also known as a single energy scan, operators set the scanning parameters. Scanning parameters include variables such as the x-ray source voltage setting, exposure time, and source filter settings.

A related technology of XRM is x-ray fluorescence ("XRF") microscopy. XRF microscopy utilizes x-rays differently than does XRM. Operators use the secondary x-ray energy emission associated with XRF, or fluorescence, to uniquely identify individual atomic elements ("Z") within the sample.

In XRM, the contrast mechanism for attenuation in the sample has two principal components in the x-ray energy range of interest called the photoelectric absorption component and the Compton scattering component. In the photoelectric absorption process, an x-ray is absorbed completely by a bound electron of an atom and ejects this electron from the atom. In the Compton scattering process, the incident x-ray loses part of its energy and gets redirected by scattering off an electron. The effects of both components contribute to the image in an XRM arising from attenuation of the illuminating x-ray beam.

The relative strength of the photoelectric absorption and Compton scattering processes is a strong function of incident x-ray energy and the atomic number Z of the atom that interacts with the x-ray. The absorption due to the photoelectric effect generally dominates at lower energies and decays in strength inversely with the fourth power of the x-ray energy. The absorption due to the Compton scattering effect becomes dominant at higher energies and has a much slower decay with x-ray energy (inversely with first power of energy).

The transition point between photoelectric and Compton scattering absorption is referred to as the "knee," where the absorption changes from decaying inversely with the fourth power of the energy to the first power. This knee is a characteristic of the atomic number Z of the atom and increases with increasing Z.

SUMMARY OF THE INVENTION

The change in x-ray absorption of a sample is a function of x-ray energy and atomic number. Samples containing materials with different atomic numbers will exhibit different absorption characteristics when subjected to x-rays at different energies. As a result, measurements of a sample taken at two distinct x-ray energies permit the separation of the sample's absorption characteristics, or x-ray attenuation, into its basic components. This type of measurement is known as "dual energy" (DE) scanning.

Operators typically perform more than one scan of a sample using different scanning parameters to reveal more information about the sample using the dual energy scanning principle. One limitation of current XRMs and their associated imaging methods is that there is no convenient way to combine and analyze the data after creating the reconstructed volume data sets for the energies for the sample.

The present invention provides a multi energy, such as dual-energy, x-ray imaging system data acquisition and image reconstruction system and method for combining separate reconstructed volumes taken at multiple energies and allowing the operator to manipulate and optimize the image contrast of a sample using the effects of DE. Operators use the system and method to achieve superior image quality and contrast over current XRM data acquisition and image reconstruction systems and methods, and to generate contrast based on the atomic number Z of the constituents of the sample.

Using the DE x-ray imaging system and its associated user interface applications, an operator performs a low energy ("LE") and high energy ("HE") x-ray scan of the same or overlapping volume of interest of the sample. The system creates a separate low-energy reconstructed tomographic volume data set from the set of low-energy projections and a separate high-energy tomographic volume data set from the set of high-energy projections.

The system subsequently performs a registration, zooming, and scaling step of the two separately reconstructed tomographic volumes to adjust for imperfections in the spatial stretch and relative position of the low-energy and high-energy tomographic datasets. This ensures the correlation of voxels in both datasets.

According to principles of the present invention, the operator then selects a desired slice of the tomographic volume that shows the features in which the operator is interested. The operator then optimizes the image contrast of the combined (mixed) dual energy image of the selected slice using a two-dimensional histogram tool, for example.

The two-dimensional histogram tool plots the intensity of pixels of the low energy slice against the intensity of pixels of the high energy slice. The intensity in the two dimensional histogram represents the number of voxels that fall into the corresponding histogram bin. The intensity is visualized by user-selectable color-maps that aid in the visibility and interpretation of the histogram.

In this histogram tool, the user interactively selects one point within the two-dimensional histogram. This selected point is also known as the pivot point. With the aid of the histogram tool, the operator manipulates the slope of a line through the pivot point in the histogram to determine the mixing parameters for low-energy and high-energy scans. In general, the pivot point does not affect the ratio of the low-energy and high-energy scans, but just the scaling of the output composite or synthetic slice. The slope of the line in the 2-D histogram determines the mixing ratio of LE and HE slices (i.e. the coefficients that are used to combine the LE and HE data). The pivot point determines an offset value. I.e.: synthetic intensity value=x*LE value+(1−x)*HE value+offset. Slope determines x and the pivot point determines offset.

After optimizing the contrast for one single slice in this manner, the same mixing operation associated with optimizing the contrast of the selected slice is applied to all slices in the low-energy and high-energy tomographic data sets. This creates a combined (mixed) volume data set from the LE and HE volume data sets with optimized image contrast throughout.

In addition to optimizing image contrast for features within a sample, usage of dual-energy can result in faster total acquisition and reconstruction time than that obtained by standard absorption techniques for certain samples.

In general, according to one aspect, the invention features a data acquisition and image reconstruction method for an x-ray imaging system. The method comprises performing a low-energy scan of a sample with an x-ray beam generated from an x-ray source using low-energy x-ray settings, performing a high-energy scan of the sample with an x-ray beam generated from an x-ray source using high-energy x-ray settings, generating a low-energy reconstructed tomographic volume data set from the low-energy scan, generating a high-energy reconstructed tomographic volume data set from the high-energy scan, registering, and preferably zooming and scaling the low-energy and high-energy tomographic data sets, rendering slice views from the low-energy and high-energy reconstructed tomographic volume data sets, and combining the low-energy and high-energy data.

In embodiments, the data acquisition and image reconstruction method operates within an objective lens-based x-ray imaging system and a projection-based x-ray imaging system in different implementations. Low-energy and high-energy data acquisitions may be performed using different x-ray detectors, x-ray lenses, sources, targets, or source filters.

In general, according to another aspect, the invention features a multi, such as dual, energy contrast tuning tool executing on a computer system of an x-ray imaging system, comprising: a low-energy window for displaying low-energy slices from a low-energy reconstructed tomographic volume data set, a high-energy window for displaying high-energy slices from a high-energy reconstructed tomographic volume data set, a slice selection window having a two-dimensional slice selection interactive graphic for selecting slices from the sample, a two-dimensional histogram showing voxel densities of low-energy versus high-energy pixel intensity values, a pivot point and line slope selection tool within the two-dimensional histogram tool, and a results window that displays synthetic (mixed) slices generated by combining the low-energy reconstructed tomographic volume data set and the high-energy reconstructed tomographic volume data set according to the pivot point and line slope selected in the two-dimensional histogram tool.

In embodiments, an operator utilizes user interface applications on a computer system to interact with and control the XRM imaging system and its components, and to perform the data acquisition, image reconstruction, and contrast optimization of a sample. Typically, the computer system has a suite of applications, such as a Scout and Scan data acquisition application to select scanning parameters and create LE and HE tomographic volume data sets of a sample, and a DE Contrast Tuning Tool application to create a DE contrast-optimized volume data set from selected LE and HE tomographic volume data sets of the sample. The user interface applications display onto a display device attached to the computer system.

In general, according to another aspect, the invention features a data acquisition and image reconstruction method for an x-ray imaging system, the method comprising: loading a sample on a sample holder of the x-ray imaging system, performing a low-energy scan by rotating the sample in a low energy x-ray beam from an x-ray source system of the x-ray imaging system, performing a high-energy scan by rotating the sample in a high energy x-ray beam from the x-ray source system, generating a low-energy reconstructed tomographic volume data set from the low-energy scan in a computer system, generating a high-energy reconstructed tomographic volume data set from the high-energy scan in the computer system, and rendering slice views from the low-energy and high-energy reconstructed tomographic volume data sets on a display device of the computer system.

It is another aspect to provide optimum single scan parameters from information associated with the DE contrast-optimized volume data set to best approximate the operator-selected settings for the DE contrast-optimized volume data set. In this way, an operator can run subsequent single-energy scans that provide improved contrast and image quality as compared to volume data sets created from current single-energy scanning methods.

It is yet a further object of the present invention to provide a DE XRM data acquisition and reconstruction system and related method that provides elemental identification between elements or compounds similar to x-ray fluorescence ("XRF") microscopy in a sample given a priori knowledge of basic sample constituents. If operators have prior knowledge of a limited range of compounds present in the sample, the x-ray pixel intensity patterns in the histogram reveal differences between elements, and also provide the ability to distinguish micro-porosity from chemical composition. For this purpose, specialized source filters utilizing specific K-edge absorption characteristics are used.

It is another aspect to calculate the atomic molarity and effective atomic number of elements within the sample from the histogram. In this way, the micro-porosity of the sample can be estimated by calculating the atomic molarity for an associated effective atomic number.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 3A, 3B and 3C are scale top, front and side views of the filter changer mechanism as employed in the systems of FIG. 1 and FIG. 2, that includes a fine adjustment control mechanism for improved filter wheel stability and placement accuracy;

DETAILED DESCRIPTION OF THE PREFERRED EMBODIMENTS

Figure 1:
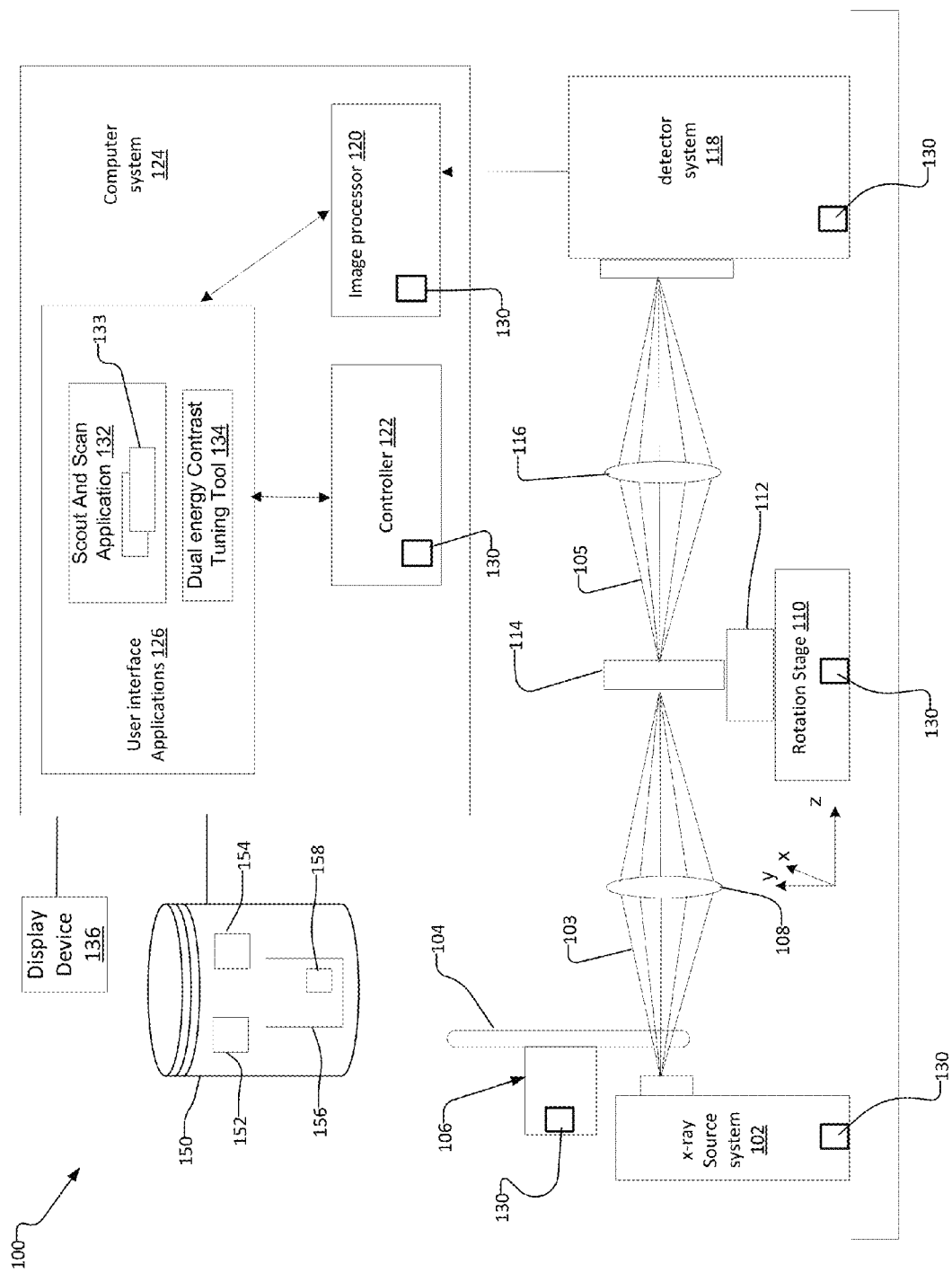
FIG. 1 is a schematic diagram of a lens-based x-ray imaging system according to an embodiment of the present invention.

FIG. 1 is a schematic diagram of a lens-based x-ray imaging system 100 ("lens-based system").

The lens-based system 100 has an x-ray source system 102 that generates an x-ray beam 103, a filter changer mechanism 106 with a filter wheel 104 for filtering the x-ray beam 103, and a rotation stage 110 with sample holder 112 for holding the sample 114. A condenser 108 placed between the x-ray source system 102 and the sample 114 focuses the x-ray beam 103 onto the sample 114.

The lens-based system 100 also has a detector system 118, and an objective lens 116 placed between the sample 114 and the detector system 118. When the sample 114 is exposed to the x-ray beam 103, the sample 114 absorbs and transmits x-ray photons associated with the x-ray beam 103. The x-ray photons transmitted through the sample form an attenuated x-ray beam 105, which the objective lens 116 images onto the detector system 118.

The detector system 118 creates an image representation, in pixels, of the x-ray photons from the attenuated x-ray beam 105 that interact with the detector system 118.

The image formed at the detector system 118 is also known as an x-ray projection, or an x-ray projection image.

The lens-based system 100 also has a computer system 124 that includes an image processor 120, a controller 122, and user interface applications 126. A display device 136 connected to the computer system 124 displays information and graphical user interfaces from the user interface applications 126. The computer system 124 loads information from, and saves information to, a database 150 connected to the computer system 124. The controller 122 has a controller interface 130 that allows an operator to control and manage components in the lens-based system 100 under software control via the computer system 124.

Operators utilize the user interface applications 126 to configure and manage components in the lens-based system 100 via the controller 122. User interface applications 126 include a scout and scan application 132 and a dual energy contrast tuning tool 134. The controller 122 controls components that have a controller interface 130. Components which have a controller interface 130 include the image processor 120, the detector system 118, the rotation stage 110, the x-ray source system 102, and the filter changer mechanism 106, in one implementation.

For selection of scanning parameters, the operator typically uses the scout and scan application 132 to configure an x-ray voltage setting and exposure time on the x-ray source system 102, and a filter setting of the filter wheel 104 of the filter changer mechanism 106. The operator also selects other settings such as the field of view of the x-ray beam 103 incident upon the sample 114, the number of x-ray projection images or slices to create for the sample 114, and the angles to rotate the rotation stage 110 for rotating the sample 114 in the x-ray beam 103.

In the multi-energy x-ray imaging of the sample 114, the operator performs at least a low-energy scan and a high-energy scan of the sample 114. The operator chooses scanning parameters associated with known x-ray absorption coefficients for compounds in the sample 114 for the low-energy and high-energy scans.

Operators utilize a number of techniques to generate the high and low energy x-ray beams for the two scans. In one example, the x-ray source system 102 generates the low-energy x-ray beam using a low energy x-ray source and generates the high-energy x-ray beam using a high energy x-ray source. In another example, the x-ray source system generates the low-energy x-ray beam using a low energy setting for an x-ray source and generates the high-energy x-ray beam using a high energy setting of the x-ray source system. In other examples the filters are used so that the x-ray source system generates the low-energy x-ray beam using a low energy filter for an x-ray source and generates the high-energy x-ray beam using a high energy filter of the x-ray source. In still a further example, different x-ray source anode targets are used so that the x-ray source system generates the low-energy x-ray beam using a low energy anode target for an x-ray source and generates the high-energy x-ray beam using a high energy anode target of the x-ray source. Finally, the x-ray source system can generate the low-energy x-ray beam using a low energy exposure time for an x-ray source and generate the high-energy x-ray beam using a high energy exposure of the x-ray source. In general, the low-energy exposure times and high-energy exposure times are different from each other and are chosen to produce datasets with sufficient signal-to-noise ratio.

Some settings, such as the scanning parameters and the number of projections for each scan, can vary between the low-energy and high-energy scans. Certain settings, however, such as the field of view and the start and end angles, must be identical or at least overlapping for the low-energy and high-energy scans. These settings are helpful for subsequent alignment and registration of the low-energy and high-energy reconstructed tomographic data sets created by their respective scans. This is a requirement for the image optimization method 900 of FIG. 9, discussed in the detailed description associated with FIG. 9 appearing later in this document.

The scout and scan application 132 has one or more dual energy templates 133. The scout and scan application 132 provides different dual energy templates 133 depending on the types of the sample 114. The dual energy templates 133 provide the same settings between the low-energy and high-energy scans required by the image optimization method 900 of FIG. 9, while allowing the operator to choose scanning parameters and other settings specific to the low-energy and high-energy scans.

Using the dual energy templates 133, the operator defines the same field of view and the same start and end angles for the low-energy and high-energy scans. The operator then defines the scanning parameters associated with the low-energy and high-energy scans, and defines other settings that can vary between the scans, such as the number of projections. The dual energy templates 133 then provide the configuration to perform the low-energy and high-energy scans of the sample 114.

During a scan, the image processor 120 receives and processes each projection from the detector system 118. The scout and scan application 132 saves the projections from the image processor 120 to later generate a reconstructed tomographic volume data set of the sample 114. The computer system 124 saves the tomographic data sets from each scan, and their associated scanning parameters and settings, to local storage on the computer system 124, or to the database 150. The computer system saves a low-energy tomographic volume data set 152 for the low-energy scan, and a high-energy tomographic volume data set 154 for the high-energy scan, to local storage or to the database 150 after their calculation.

The operator uses the dual energy contrast tuning tool 134 for optimizing the image contrast of the sample 114. Using the dual energy contrast tuning tool 134, the operator loads the low-energy tomographic volume data set 152 and high-energy tomographic volume data set 154. The operator then selects a slice within the datasets, and selects information for optimizing the image contrast of the selected slice. The operator then applies this information to optimize the image contrast and create a combined or synthetic volume data set 156.

Because the combined volume data set 156 contains slices with optimized image contrast, the combined volume data set 156 is also referred to as an optimized combined volume data set.

Once the operator has created the combined volume data set 156, the operator optionally uses use the dual energy contrast tuning tool 134 to calculate optimum single-scan parameters 158 from the scanning parameters associated with the creation of the combined volume data set 156. This is especially useful if the operator intends to perform runs against several samples to produce the same approximate contrast results. In this way, the operator can apply the optimum single-scan parameters 158 to the lens-based system 100 to perform a subsequent single-energy scan of the same sample 114, or of a new sample with similar elemental composition.

The calculation of optimal single-scan parameters is discussed in more detail in the detailed description associated with method 938 in FIG. 10B, appearing later in this document.

Figure 2:
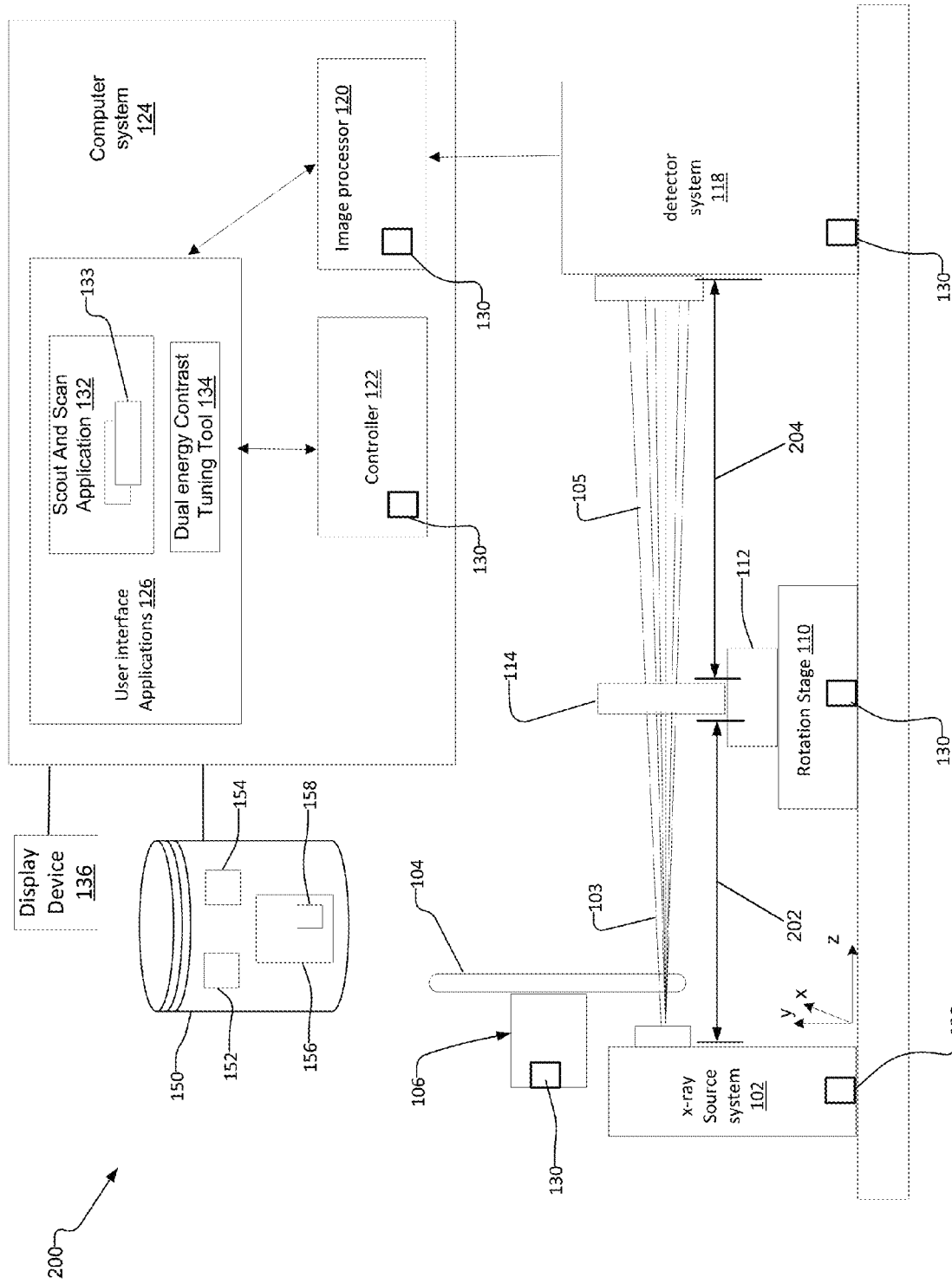
FIG. 2 is a schematic diagram of a projection-based x-ray imaging system according to another embodiment of the present invention.

FIG. 2 is a schematic diagram of a projection-based x-ray imaging system 200 ("projection-based system") according to another embodiment of the present invention. The projection-based system 200 is similar in structure to the lens-based system 100 and has nearly identical behavior but is typically lower performance in terms of magnification levels.

The projection-based system 200 eliminates the condenser 108 and objective lens 116 of the lens-based system 100. Otherwise, the projection-based system 200 has the same components as the lens-based system 100, and operators utilize the projection-based system 200 and its components in an identical fashion to the lens-based system 100 for creating x-ray projections and reconstructed tomographic volume data sets of the sample 114.

The projection-based system 200 does not rely on lenses to create a magnified transmission image of the sample 114. Instead it creates a magnified point projection image of the sample 114 by utilizing a small x-ray source spot of the x-ray source 102 projected on the detector system 118. The magnification is achieved by positioning the sample 114 close to the x-ray source 102, in which case the resolution of the projection based system 200 is limited by the spot size of the x-ray source. A magnified projection image of the sample 114 is formed on the detector system 118 with a magnification that is equal to the ratio of the source-to-sample distance 202 and the source-to-detector distance 204. Another way to achieve high resolution in the projection-based system 200 is to employ a very high resolution detector system 118 and to position the sample 114 close to the detector, in which case the resolution of the x-ray image is limited by the resolution of the detector system 114.

For adjusting the magnification of the image, the operator utilizes the user interface applications 124 on the computer system 124 to adjust the source-to-sample distance 202 and the source-to-detector distance 204. The operator adjusts these distances, and achieves the desired magnification, by moving the rotation stage 100 via the controller 122. The x-ray detector system 118 also provides the ability to adjust the field of view on the sample by changing the pixel size within the x-ray detector system 118, according to some implementations.

FIG. 3A is a scale top view of a filter changer mechanism 106 as employed in the lens-based system 100 in FIG. 1 and the projection-based system 200 in FIG. 2. Filter changer mechanism 106 has a filter wheel 104 that holds filters in each of the circular ports 104-1 arrayed around the periphery of the wheel.

FIG. 3B and FIG. 3C are scale front and side views of the filter changer mechanism 10. The filter changer mechanism 106 features a fine adjustment control mechanism 302 for improved stability and placement accuracy of the filter wheel 104.

The filter wheel 104 has the ports 104-1 that typically include filters for filtering the x-ray beam 103. Operators select different filters under software control using the user interface applications 126 and the controller 122 of the computer system 124 in FIG. 1 and FIG. 2.

In response to operator selection of a filter associated with an aperture 104-1, the controller 122 signals the filter changer mechanism 106 to rotate the filter wheel 104 to the aperture 104-1 in response to the selection. When the lens-based system 100 in FIG. 1 and the projection-based system 200 in FIG. 2 transmit the x-ray beam 103, the x-ray beam 103 passes through the filter associated with the selected aperture 104-1.

It should be noted that in FIGS. 1 and 2, the filter changer mechanism 106 is shown between the source 102 and sample 114. In other examples, the filter changer mechanism 106 is located between the sample 114 and detector system 118.

Figure 4:
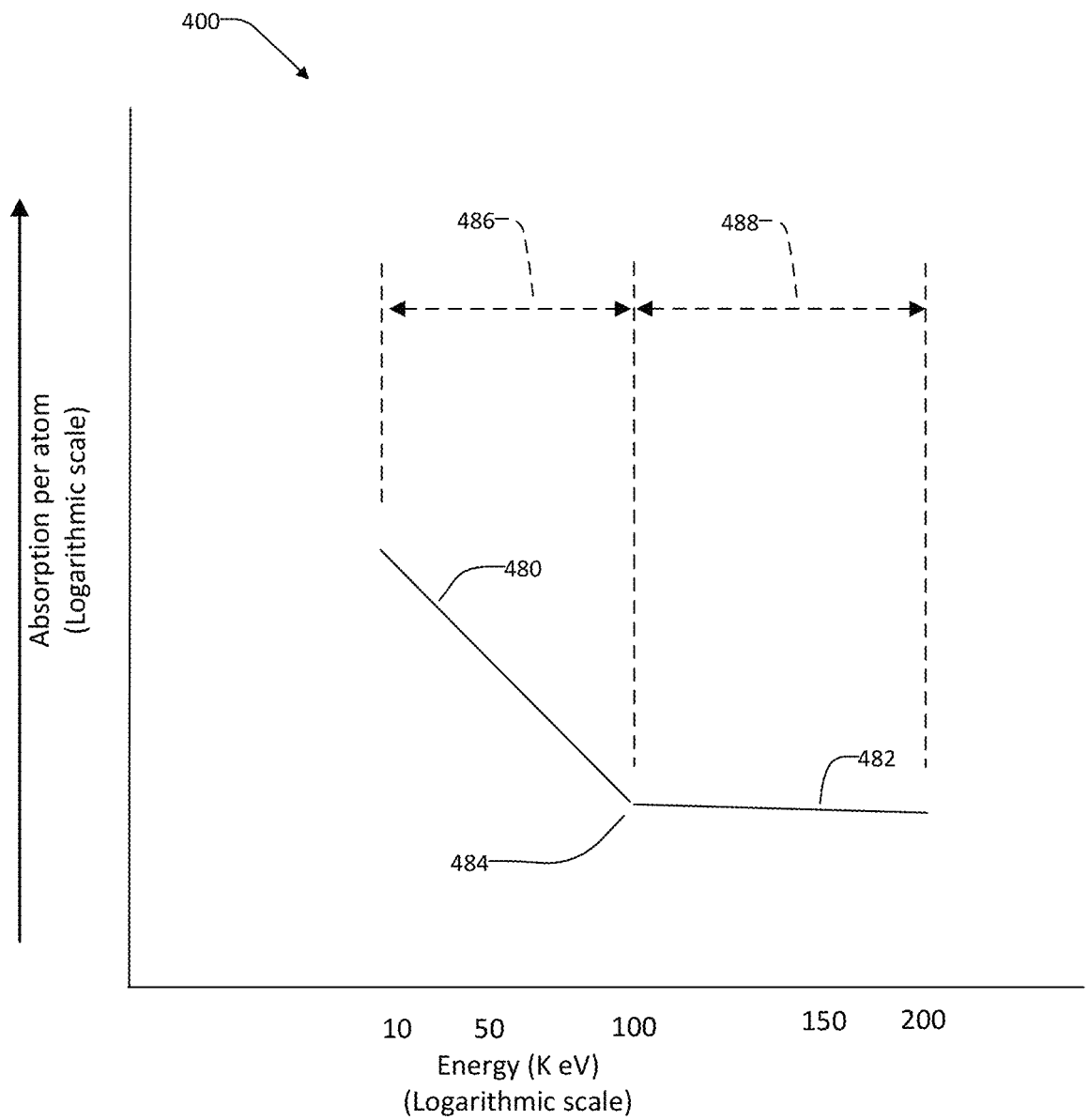
FIG. 4 is a typical x-ray absorption versus x-ray energy curve for low-Z elements such as Calcium (Z=20) that provides a rationale for utilizing dual-energy x-ray imaging of a sample to isolate properties within the sample.

FIG. 4 is a typical x-ray absorption versus x-ray energy plot 400 ("absorption plot") for low-Z elements such as Calcium (Z=20) that provides a rationale for utilizing dual-energy x-ray imaging of a sample to isolate properties within the sample. Both axes are plotted using a logarithmic scale. Dual-energy x-ray imaging of a sample utilizes the crossover in absorption and scattering behavior when a sample 114 is irradiated with low-energy and high-energy x-rays.

Low-Z elements typically include Hydrogen (H=1) to Iron (Fe=26), and high-Z elements are elements whose atomic numbers are larger than Iron. With respect to dual-energy x-ray imaging, low-Z elements have different absorption plots 400 than high-Z elements.

The absorption plots 400 of low-Z elements have a LE absorption section 480 and a HE absorption section 482, separated by a knee or inflection point 484. The LE absorption section 480 is associated with applied x-ray energy in the LE scan range 486, and the HE absorption section 482 is associated with applied x-ray energy in the HE scan range 488.

For a given x-ray energy and element with atomic number Z, the LE absorption section 480 scales inversely with Z^4 over the LE scan range 486, and the HE absorption section 482 scales inversely linearly with Z over the HE scan range 488. The x-ray absorption in the LE absorption section 480 is typically attributable to absorption associated with the photoelectric effect, whereas the x-ray absorption in the HE absorption section 482 is typically attributable to Compton scattering.

For all Z, the x-ray energy associated with the knee 484 of their absorption plots 400 increases with increasing Z. The absorption plots 400 for high-Z elements have a less-discernible knee to that of low-Z elements. Their LE scan ranges 486 and HE scan ranges 488 increase with increasing Z, and K-edge absorption transitions become more of a factor. However, the DE x-ray imaging techniques also apply to high-Z elements, such as Gold and Iodine, by using scanning parameters and filters specific to each element that limit or utilize the effect of K-edges in their absorption plots 400.

Figure 5:
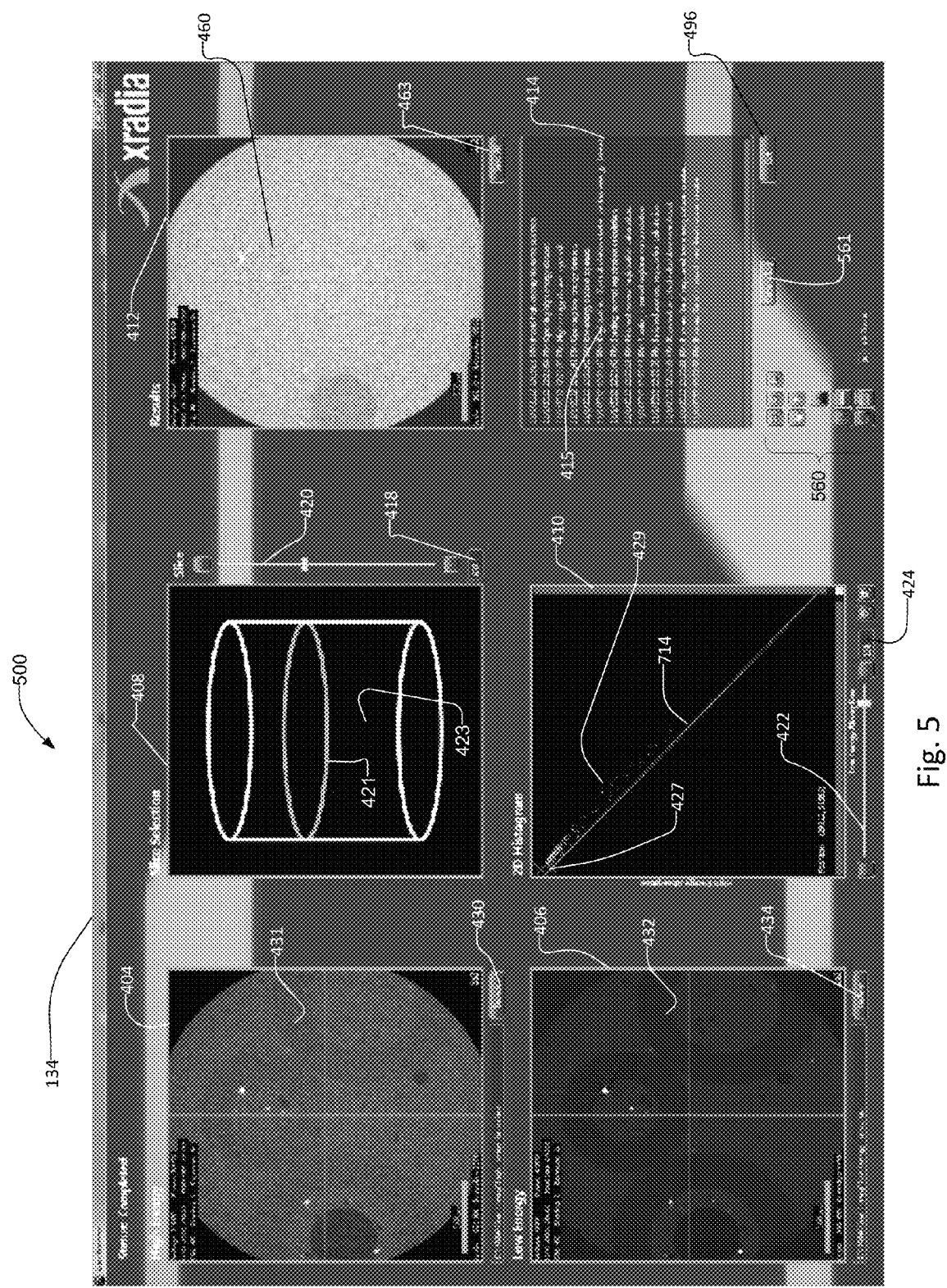
FIG. 5 illustrates the graphic user interface of a dual energy contrast tuning tool application, displaying exemplary optimized contrast information associated with a sample containing one atomic element.

FIG. 5 illustrates the graphical user interface 500 from the dual energy contrast tuning tool 134, displaying exemplary optimized contrast information associated with a sample. The dual energy contrast tuning tool 134 has a high energy window 404 for selection and display of a slice from a high-energy tomographic volume data set 154 of a sample, and a low energy window 406 for selection and display of a slice from a low-energy tomographic volume data set 152 of the same sample. The high-energy tomographic volume data set 154 and the low-energy tomographic volume data set 152 were generated using the x-ray imaging systems in FIG. 1 and FIG. 2.

The high energy window 404 has a high energy tomographic volume data set selector 430, and the low energy window 406 has a low energy tomographic volume data set selector 434. The operator uses the high energy tomographic volume data set selector 430 to open a file browser dialog for selection of a high energy tomographic volume data set 154 on the computer system 124 or on the database 156. The operator uses the low energy tomographic volume data set selector 434 to open a file browser dialog for selection of a low energy tomographic volume data set 152 on the computer system 124 or on the database 156.

The dual energy contrast tuning tool 134 also has a slice selection window 408, a 2-D histogram window 410, a results window 412 that displays a synthetic or optimized slice image 460, and a log window 414. The slice selection window 408 has an interactive graphic 423 for displaying an operator-selected slice from the low energy tomographic volume data set 152 and the high energy tomographic volume data set 154. The interactive graphic 423 has a slice selection display 421. The slice selection window 408 has a slice selector slider bar 420, and a slice number indicator 418.

The 2-D histogram window 410 includes a 2-D histogram 429 showing voxel or pixel intensities resulting from the plot of the pixel intensities for the LE slice 431 versus the pixel intensities of the HE slice 432. An operator uses the 2-D histogram window 410 to interactively determine the mixing parameters of the LE slice 432 and HE slice 431.

The operator interactively determines the mixing parameters of the LE slice 432 and HE slice 431 by selecting a pivot point 427 and angle within the 2-D histogram 429. In response to the selection of the pivot point 427 and angle 424, the 2-D histogram window 410 draws the slope of a line 714 through the pivot point 427 at the angle within the 2-D histogram 429.

In general, the pivot point does not affect the ratio of the low-energy and high-energy scans, but just the scaling of the output composite or synthetic slice. The slope of the line in the 2-D histogram 429 determines the mixing ratio of LE and HE slices (i.e. the coefficients that are used to combine the LE and HE data). The pivot point 427 determines an offset value. I.e.: synthetic intensity value=x*LE value+(1−x)*HE value+offset. Slope determines x and the pivot point determines offset.

The operator chooses the angle via an angle selector slider bar 422, and an angle number indicator 424 reflects the value of the angle selected in degrees. The pivot point 427 is selected by clicking on a point within the 2-D histogram. The shown brightness or intensity in the 2-D histogram 429 is a measure of the number of voxels in the slice with given pixel intensity of the LE slice 432 versus HE slice 431 pixel intensities. The 2-D histogram intensity is displayed with user selectable color maps that determine the colors representing different intensities.

The 2-D histogram densities are scaled logarithmically to make sure even single pixels can be seen as points on the 2-D histogram 429 to ensure that data that corresponds to small features on the slice is still visible. The operator uses the distribution of pixels on the 2-D histogram as a starting guide to select the pivot and angle of the line 714. The results window 412 displays a synthetic slice 460 computed through settings of the line 714 in the 2-D histogram window 410. The log window 414 displays log information 415 associated with the operations of the dual energy contrast tuning tool 134.

Once the operator has selected the high energy tomographic volume data set 154 and the low-energy tomographic volume data set 152, the computer system 124 auto-aligns, registers, and scales the high energy tomographic volume data set 154 and the low-energy tomographic volume data set 152 with each other, and in magnification, in response to the selections.

The operator then uses the slice selection window 408 to select a slice within the high energy tomographic volume data set 154 and the low-energy tomographic volume data set 152. Using the slice selector slider bar 420, with the aid of the interactive graphic 423, the operator selects a slice, and the slice selection display 421 of the interactive graphic provides a visual indicator of the selected slice relative to the total number of slices available. The slice number indicator 418 also displays the slice number of the selected slice.

The selected slice is an abstraction or device used by the dual energy contrast tuning tool 134 to select a common slice within the high energy tomographic volume data set 154 and the low-energy tomographic volume data set 152. The computer system 124 uses the information associated with the selected slice to compute the 2-D histogram 429 of high-energy pixel intensity versus low-energy pixel intensity values for the selected slice. The points displayed on the 2-D histogram 429 form visually-distinct clusters of pixel densities associated with elements in the sample for the selected slice. Then, the operator selects a pivot point of interest and angle within the histogram, and the computer system 124 computes the synthetic slice image 460 using the information associated with the point and angle selections. This is discussed in more detail in the detailed description associated with the exemplary histogram 800 in FIG. 8, appearing later in this document.

When the operator has selected a slice in the slice selection window 408, the high energy window 404 displays a high-energy ("HE") slice 431 from the high-energy tomographic volume data set 154 associated with the slice selection, and the low energy window 406 displays a low-energy ("LE") slice 432 of the low-energy tomographic volume data set 152 associated with the slice selection. The computer system 124 automatically creates the histogram 429, and the 2-D histogram window 410 displays the histogram 429, in response to the slice selection.

The 2-D histogram window 410 has an angle selection slider bar 422, and an angle number indicator 424. When the 2-D histogram window 410 displays the histogram 429, the operator selects a point of interest, or pivot point 427 within the histogram 429 for image contrast optimization of the selected slice. When the operator has selected the point of interest 427, the angle selection slider bar 422 becomes operable. Using the angle selection slider bar 422, the operator selects an angle within the histogram 429, and the angle number indicator 424 displays the angle, in degrees, in response to the angle selection.

The computer system 124 draws a ratio calculation line 714 through the operator-selected point of interest 427 and angle in the histogram 429. The ratio calculation line 714 is a visual aid to the operator to display the ratio between the high-energy pixel intensity versus the low-energy pixel intensity information that the computer system 124 will use from the 2-D histogram 429 when optimizing the selected slice. The results window 412 displays the synthetic slice 460 that the computer system 124 calculates in response to the operator-selected point of interest 427 and angle in the 2-D histogram 429.

In a continuous fashion, whenever the operator selects a different slice in the slice selection window 408, the high energy window 404 updates the display of the high-energy slice 431, and the low energy window 406 updates the display of the low-energy slice 432, in response to the slice selection. In a similar fashion, the computer system 124 computes a new histogram 429 for the selected slice, and the 2-D histogram window 410 displays the 2-D histogram 429, and the results window 412 displays a synthetic slice 460 in response to the operator-selected point of interest 427 and angle in the 2-D histogram 429.

The synthetic slice 460 is a contrast-optimized slice. Once the operator is satisfied with the synthetic slice 460, the operator selects the save button 463 to apply the image contrast information associated with the synthetic slice 460 to all slices in the high energy tomographic volume data set 154 and the low-energy tomographic volume data set 152, creating a new, combined tomographic volume data set. Because the combined volume data set is generated using contrast information associated with the synthetic slice 460, the combined volume data set is also known as an optimized combined tomographic volume data set 156. The computer system 124 saves the optimized combined tomographic volume data set 156 to local storage, or to the database 156.

Figure 6A:
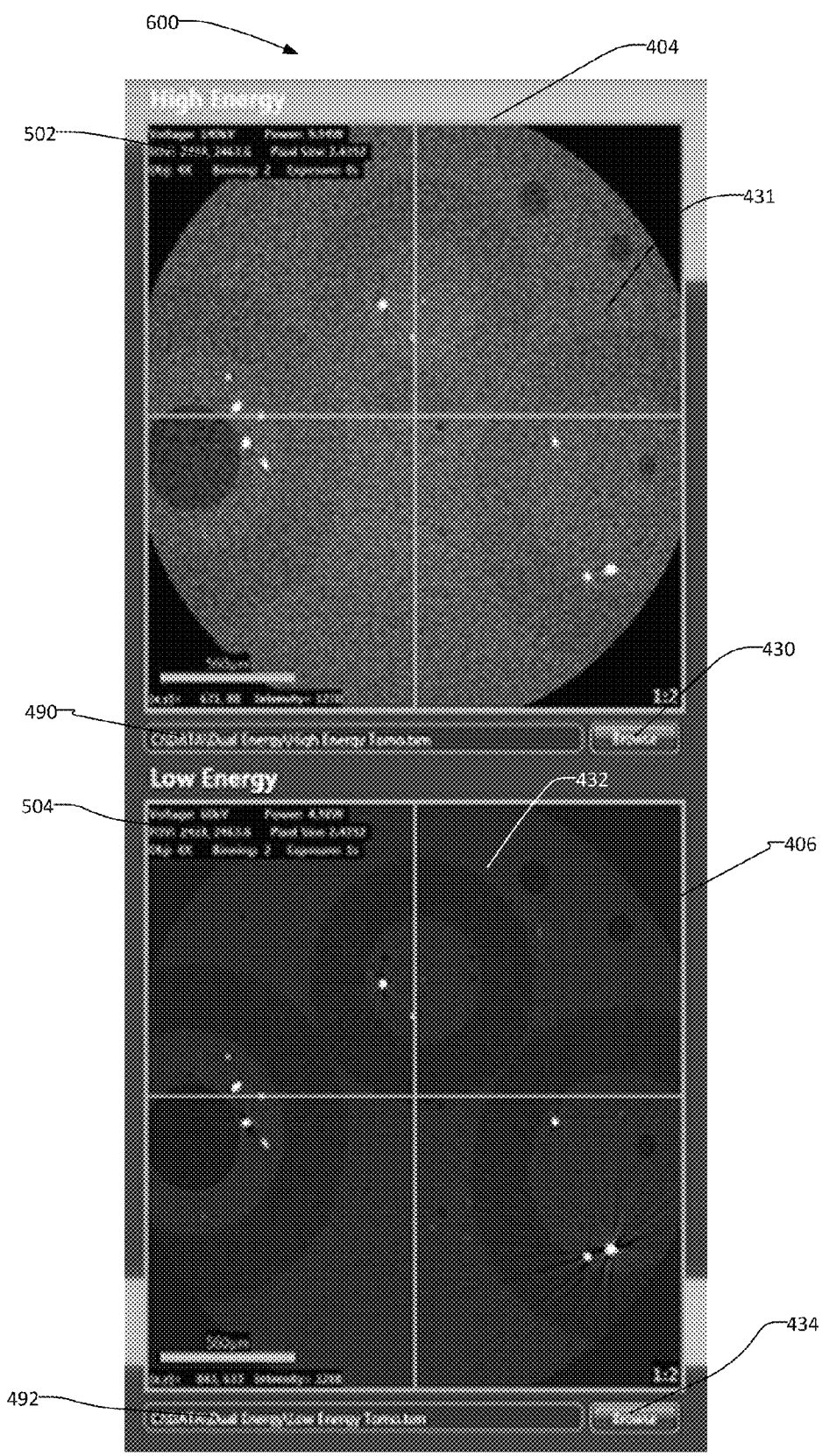
FIG. 6a is a magnified view of the dual energy contrast tuning tool in FIG. 5, showing details of the low energy window and the high energy window.

FIG. 6a is a magnified view 600 of the dual energy contrast tuning tool in FIG. 5, showing details of the low energy window 406 and the high energy window 404. The high energy window 404 also has a high energy filename indicator 490 that displays the filename associated with the selected high energy tomographic volume data set 154. The high energy window 404 also displays high-energy scanning parameters 502 overlaid upon the high energy slice 431.

The low energy window 406 also has a low energy filename indicator 492 that displays the filename associated with the selected low energy tomographic volume data set 152. The low energy window 406 also displays high-energy scanning parameters 504 overlaid upon the low energy slice 432.

Figure 6B:
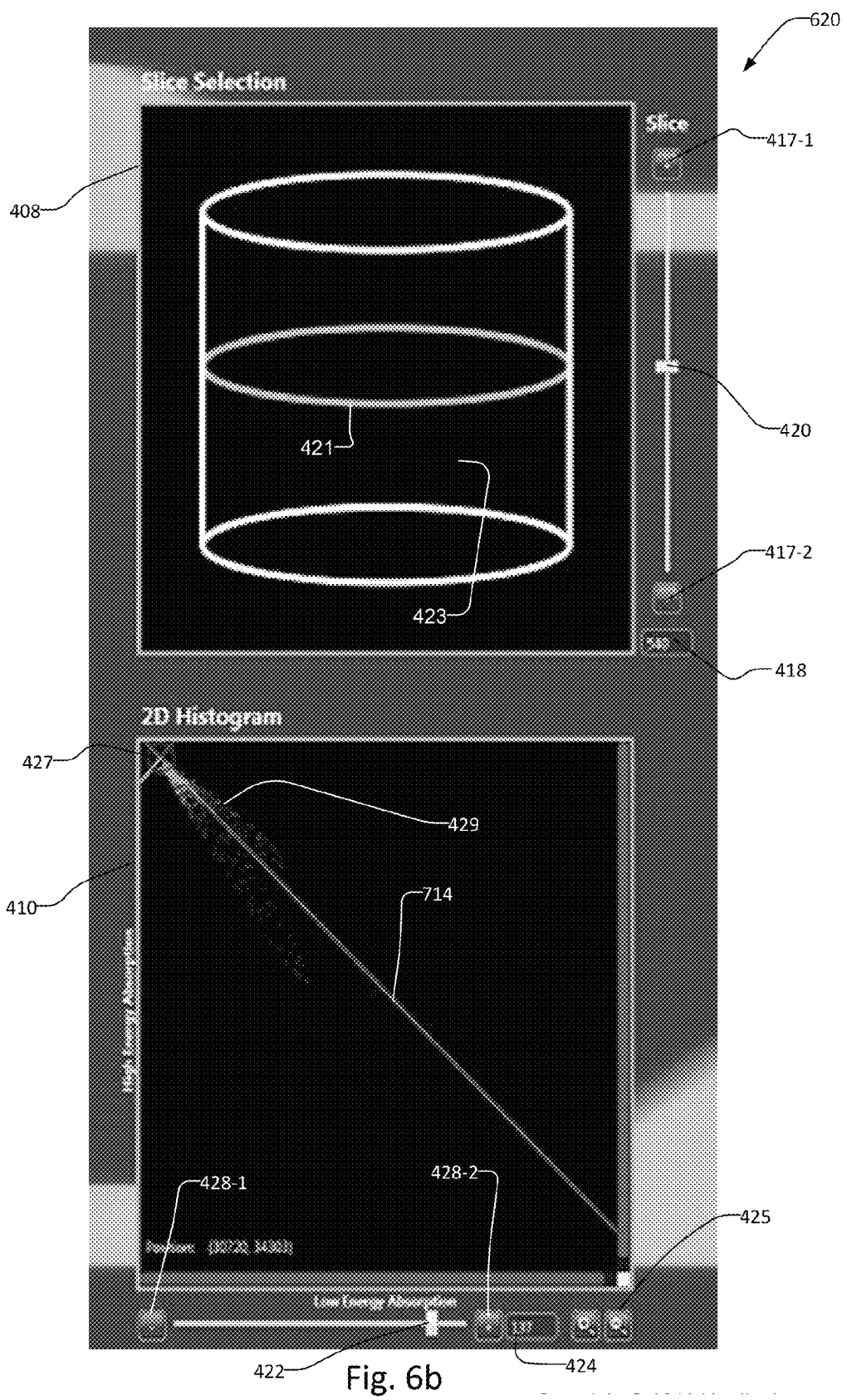
FIG. 6b is a magnified view of the dual energy contrast tuning tool in FIG. 5, showing details of the slice selection window and the histogram window.

FIG. 6b is a magnified view 620 of the dual energy contrast tuning tool 134 in FIG. 5, showing details of the slice selection window 408 and the histogram window 410. The slice selection window 408 also has slice selection buttons 417-1 and 417-2 that increment and decrement, respectively, the slice selection. The number of the selected slice displayed on the slice number indicator 418 updates in response to the selection, the slice selection display 421 of the interactive graphic 423 updates in response to the selection, and the slice selection slider bar 420 updates in response to the selection.

The histogram window 410 also has angle selector buttons 428-2 and 428-1 that increment and decrement, respectively, the selected angle in the histogram 429. The angle displayed on the angle number indicator 424 updates in response to the selection, and the angle selection slider bar 422 updates in response to the selection.

The histogram window 410 also has zoom in/out buttons 425 for magnifying portions of the histogram 429 displayed in the histogram window 410. This allows the operator to visualize individual points within the histogram 429 for selection of the point of interest 427.

Figure 6C:
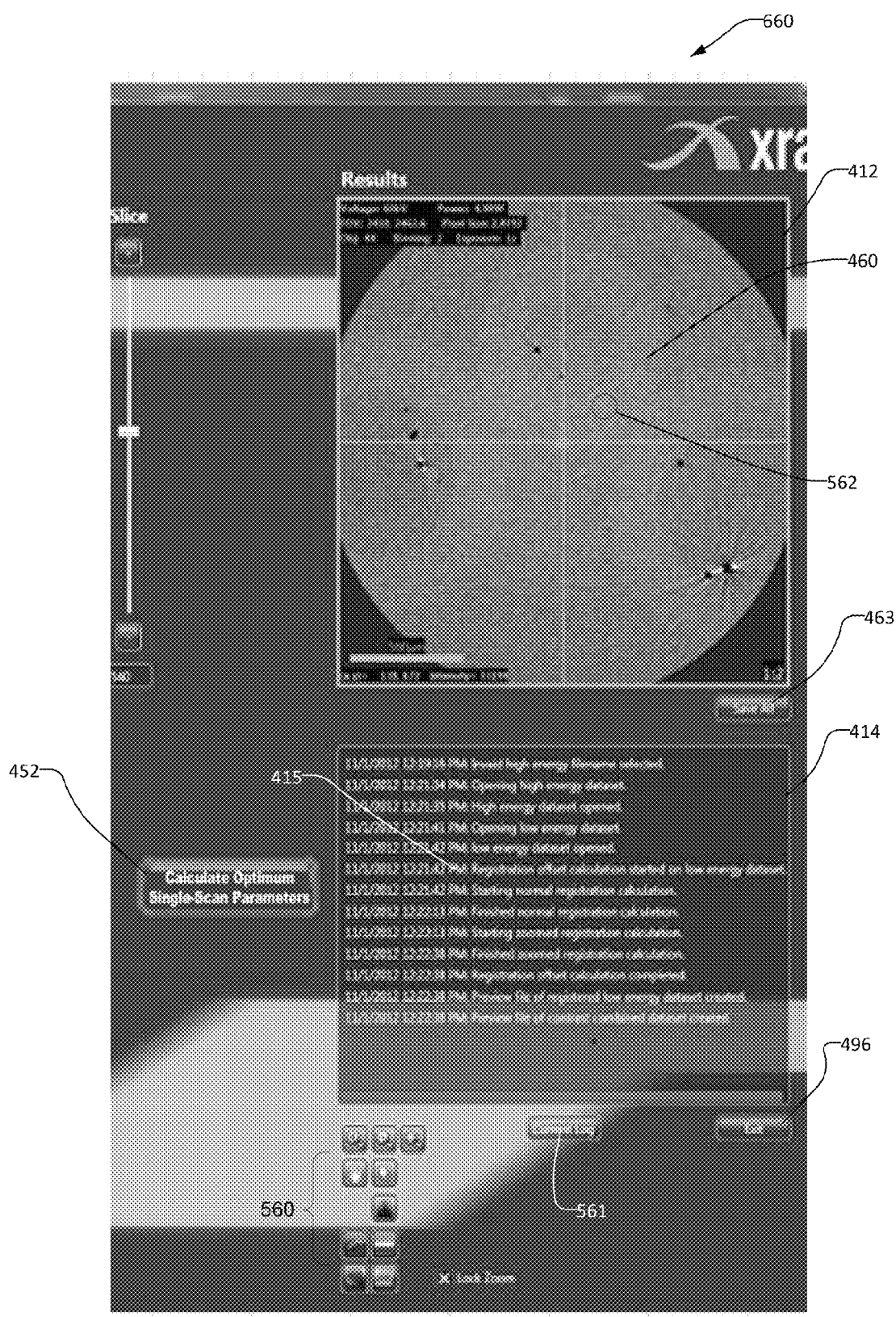
FIG. 6c is a magnified view of the dual energy contrast tuning tool in FIG. 5, showing details of the results window and the log window during optimal single scan parameter selection.

FIG. 6c is a magnified view 660 of the dual energy contrast tuning tool 134 in FIG. 5, showing details of the results window and the log window during optimal single scan parameter selection. After the operator creates the synthetic slice 460, the results window displays the synthetic slice associated with the optimization actions the operator performs within the histogram 429 in the histogram window 410. In addition, the results window 460 enables the user to select an optimized point 562 on the synthetic slice 460. Using the information associated with the optimized point 562, the computer system 124 creates optimum single-scanning parameters that the operator can apply to the same sample, or to a new sample with similar elemental composition.

When the operator selects the optimized point 562 on the synthetic slice 460, the dual energy contrast tuning tool 134 enables selection of a create optimum single scan parameters button 452. The computer system creates optimum single scanning parameters associated with the optimized point 562 in response to the selection. The computer computes the scan settings for the optimum single scan to approximate the contrast in the optimized point 562 as well as possible. This is accomplished by comparing transmission values through the optimized point 562 in the LE and HE data sets and picking the optimized single scan values from a look up table.

The dual energy contrast tuning tool 134 also has an annotation palette 560 for performing statistical operations, and zooming in/out of a selected window. The log window also has a log button 561 for enabling the display of log information 415 in the log window 414. The dual energy contrast tuning tool 134 also has an exit button 496 for exiting the dual energy contrast tuning tool 134.

Figure 7A:
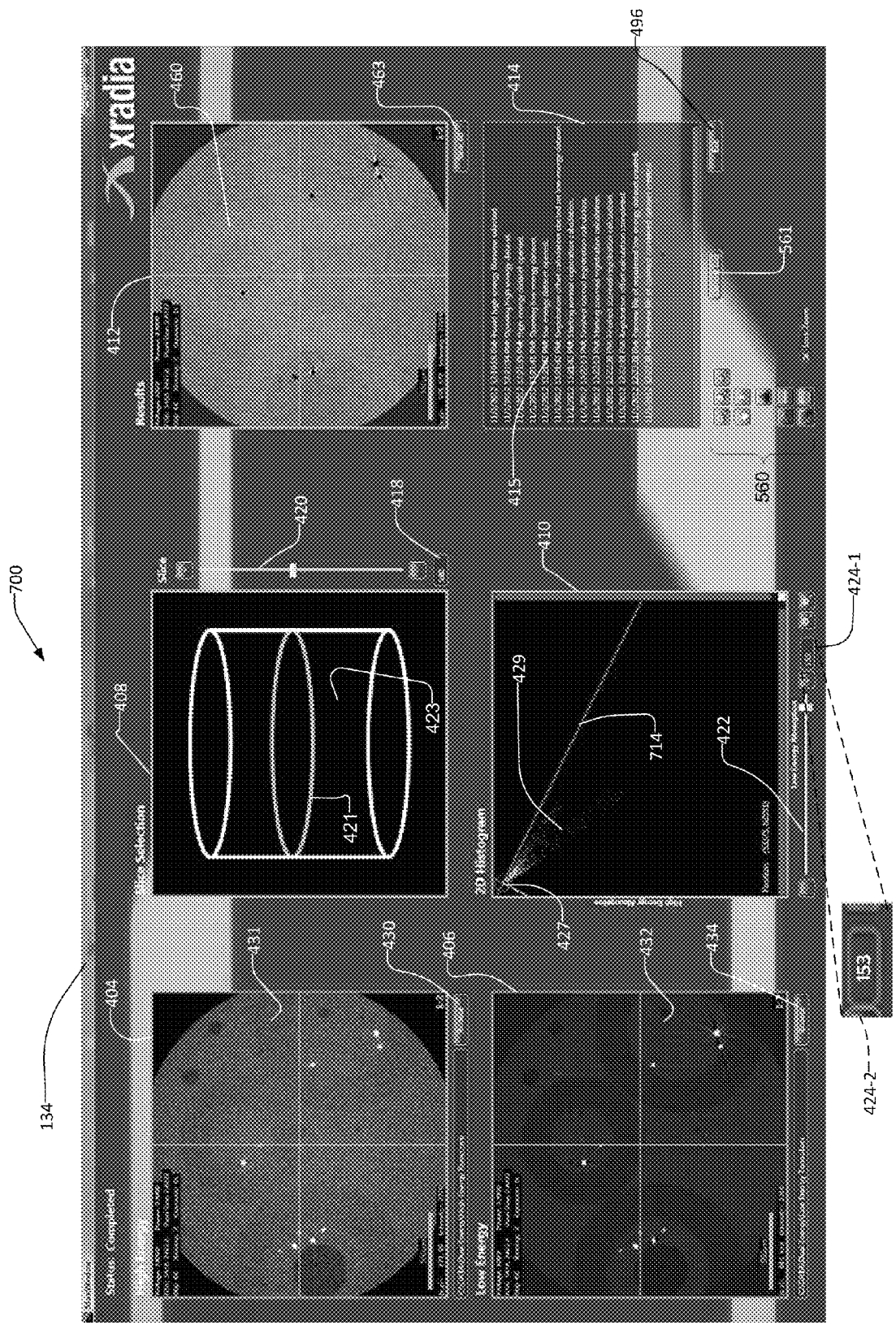
FIGS. 7a-7c illustrate the graphical user interface of the dual energy contrast tuning tool, displaying exemplary optimized contrast information associated with a sample containing Platinum and Lead, with selected contrast optimization angles of 153 degrees, 137 degrees, and 115 degrees, respectfully.
Figure 7B:
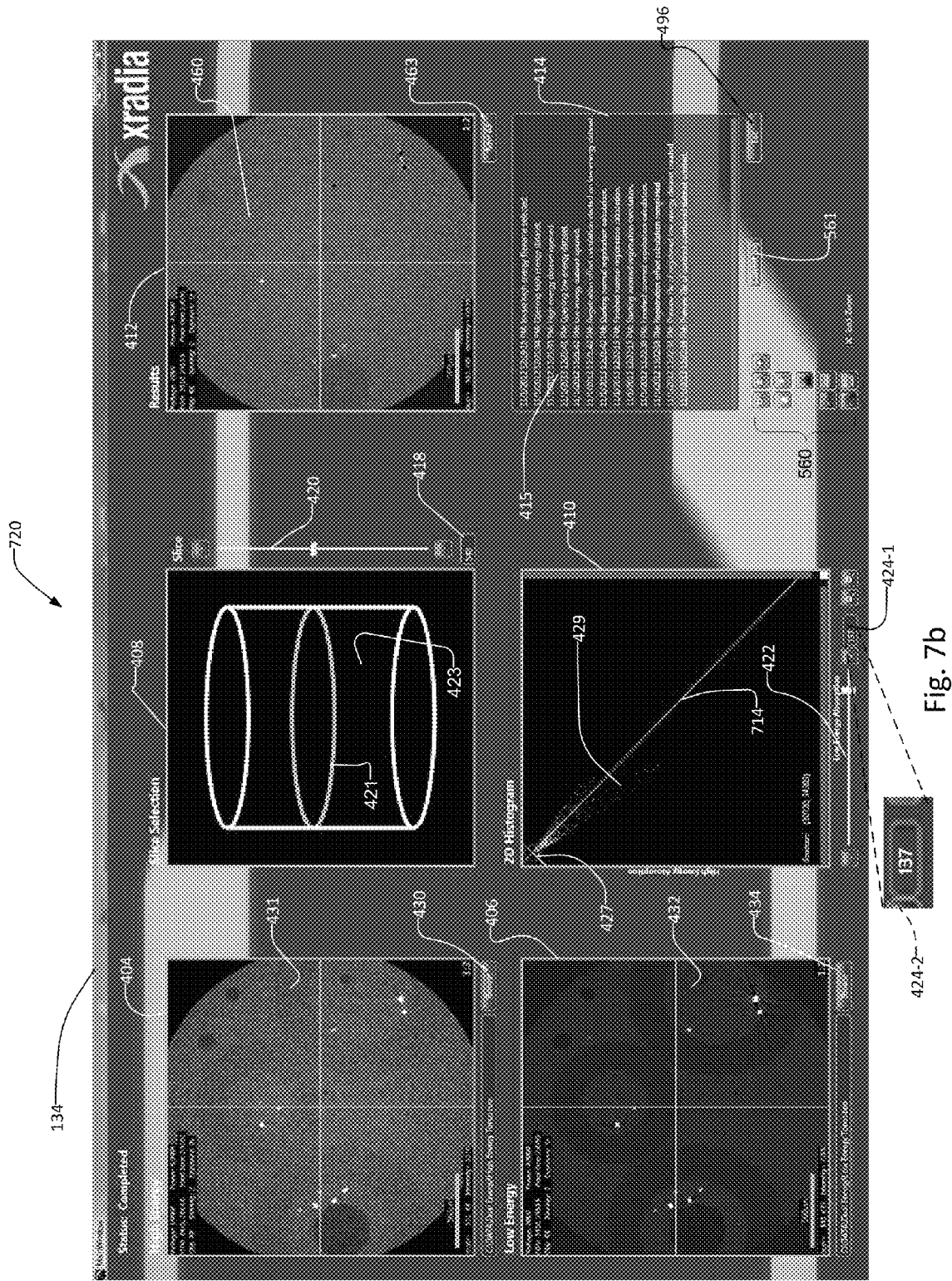
Figure 7C:
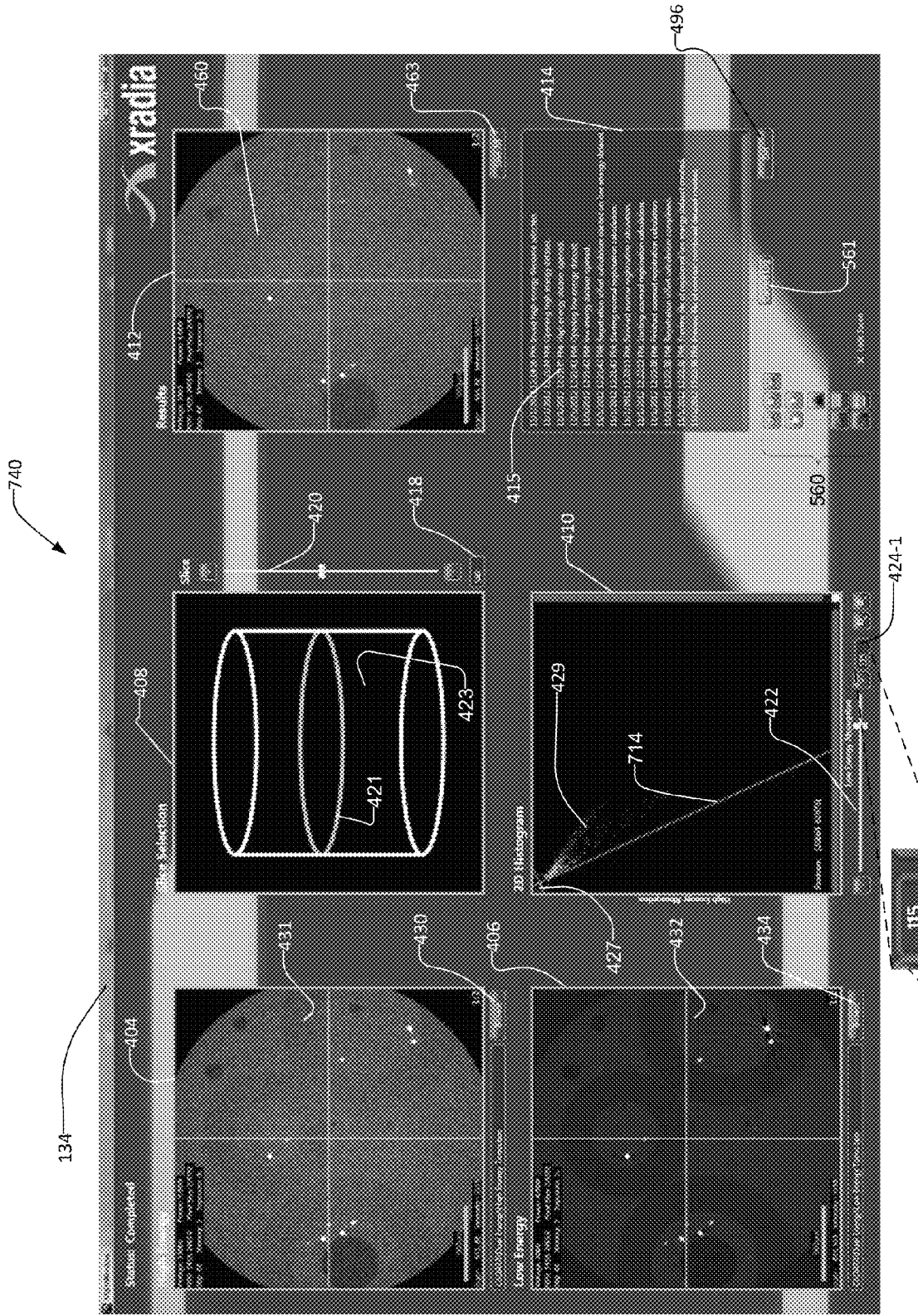

FIG. 7a-7c illustrate the dual energy contrast tuning tool 134, displaying exemplary optimized contrast information associated with a sample containing Platinum and Lead, with selected contrast optimization angles of 153 degrees, 137 degrees, and 115 degrees, respectfully. The figures illustrate the separation of lead from platinum in a calibration sample through selection of the correct pivot point 427 and angle. The contrast information of the synthetic slice 460 changes in response to the selection, with the different particles changing from black to white. In the figures, angle number indicator 424-2 is a magnified version of angle number indicator 424-1 for improved visibility. The computer system 124 draws the ratio calculation line 714 through the selected point of interest or pivot point 427 and selected angle.

Figure 7D:
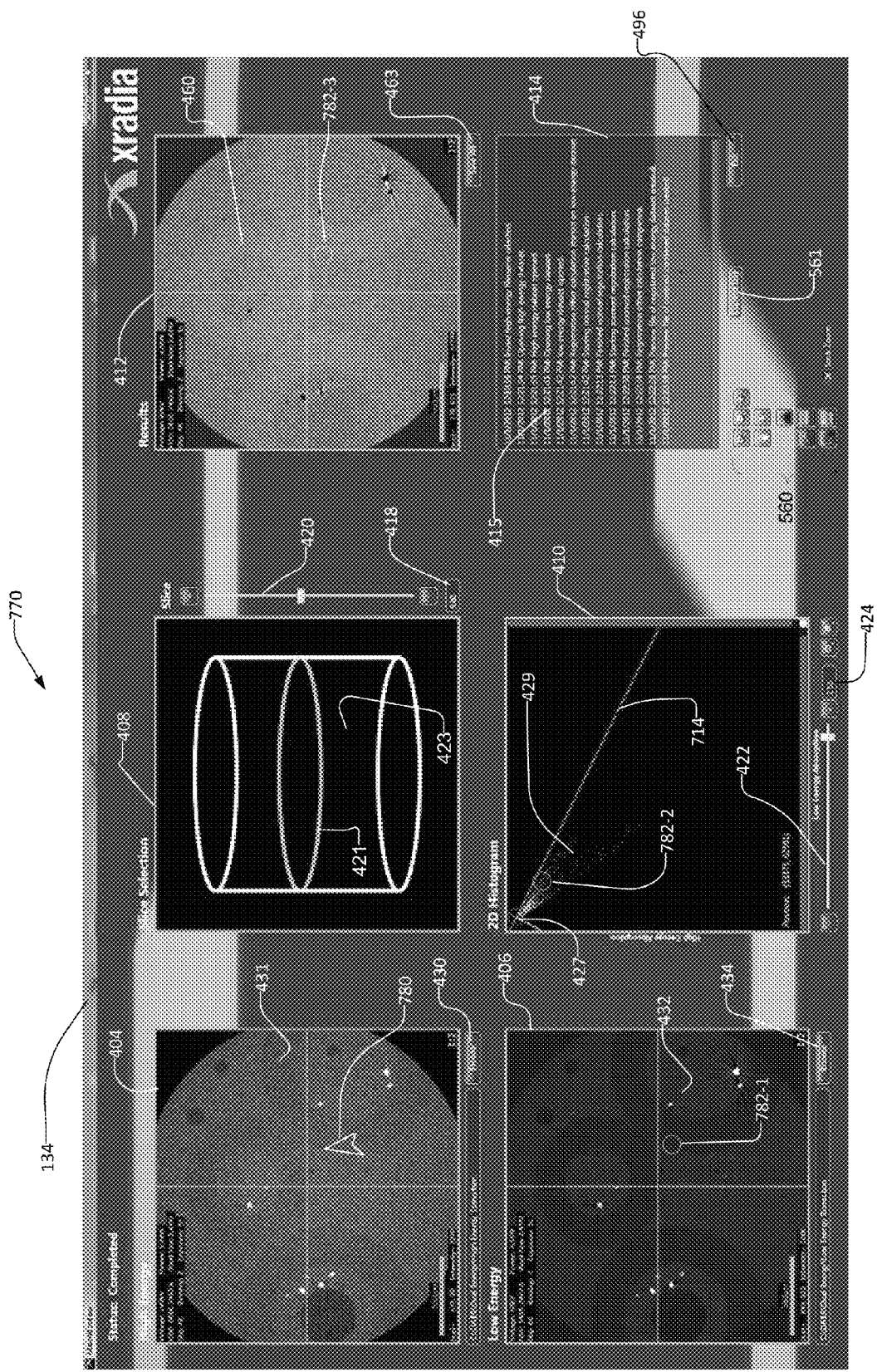
FIG. 7d illustrates the dual energy hover tool 770 within the context of the dual energy contrast tuning tool 134.

FIG. 7d illustrates the dual energy hover tool 770 within the context of the dual energy contrast tuning tool 134. The dual energy hover tool 770 provides real-time correlation between the images shown in the LE window 404, the HE window 406, the results window 412 and the 2-D histogram window 410.

When the operator uses a pointing device such as a mouse and hovers over a pixel or voxel in the LE slice 432 or HE slice 431 or synthetic slice 460, the point corresponding to this voxel in the 2-D histogram is highlighted. This interactive feature allows the operator to locate where different constituents of the sample are located on the 2-D histogram 429.

In one example, pointer icon 780 points to the location where the operator directs a pointing device hover operation. The location is a point in the HE slice 431. A selection of a point during a mouse hover event is also known as an indication. In response to the indication, the dual energy hover tool 770 calculates and highlights the LE slice associated points 782-1, the 2-D histogram associated point 782-2, and the synthetic slice associated point 782-3.

In another example, the operator indicates a point in the 2-D histogram 429 corresponding to one combination of LE and HE voxel intensities. In response to the indication, all voxels in the LE slice 432, the HE slice 431 and the synthetic slice 460 that have the corresponding LE and HE intensities will be highlighted. This allows the operator to localize different constituents from the 2-D histogram 429 in the image data.

Figure 8:
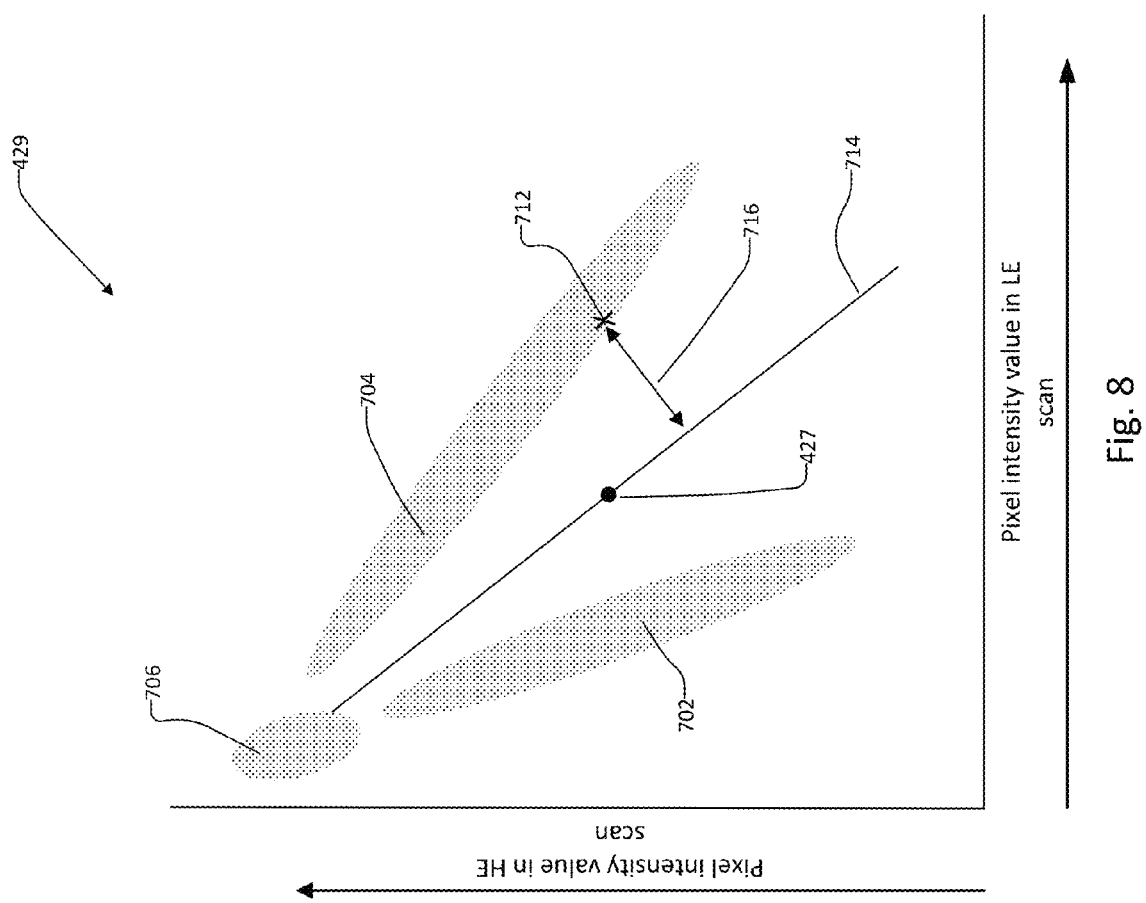
FIG. 8 schematically shows an exemplary histogram of high-energy x-ray absorption versus low-energy x-ray absorption for a sample having two elements.

FIG. 8 schematically illustrates an exemplary 2-D histogram 429 of high-energy x-ray absorption versus low-energy x-ray pixel intensities for a sample 114 having two constituents with different effective atomic number Z in addition to air. The 2-D histogram 429 displays information associated with three visually-distinct clusters of pixel intensities associated with x-ray absorption of three materials: an air pixel intensity cluster 706, a low-Z element pixel intensity cluster 702, and a high-Z element pixel intensity cluster 704.

The operator selects a pivot point 427 and angle within the 2-D histogram 429, and the computer system 124 draws the ratio calculation line 714 through the pivot point 427 and angle selection indicated by the angle number indicator 424. The ratio calculation line 714 provides the ratio of high-energy to low-energy pixel intensity for the computer system 124 to use when creating the synthetic slice 460 for the operator-selected slice in the slice selection window 408. The operator uses the pivot point 427 and angle selection to isolate properties in the sample 114.

In the example, the operator wishes to provide separation between a low-Z element associated with the low-Z pixel intensity cluster 702, and a high-Z element associated with the high-Z element pixel intensity cluster 704. Each point on the pixel intensity clusters is a voxel 712.

The color of the points on the 2-D histogram 429 is a measure of how many voxels are in this bin (i.e. which voxels have the same LE and the same HE x-ray pixel intensity values). The 2-D histogram window 410 uses an offset logarithmic scale when displaying the 2-D histogram 429 to make sure even single pixels show up in the 2-D histogram 429 as recognizable points.

The computer system 124 calculates the synthetic slice 460 from the pivot point 427 and angle selection within the 2-D histogram 429. Specifically, the computer system 124 iterates over all voxels 712 in the 2-D histogram 429, and calculates voxel offset 716, or distance between the voxel 712 and the ratio calculation line 714 in the 2-D histogram 429, for each voxel 712.

The voxel offset 716 is counted positive if the voxel 712 lies on one side of the ratio calculation line 714, and negative if the voxel 712 lies on the opposite side of the ratio calculation line 714. From the set of voxel offsets 716, the computer system 124 creates the synthetic slice 460.

When the computer system 124 saves the synthetic slice 460, the computer system 124 also saves other related information, including the 2-D histogram 429, a binary mask image containing 0 and 1 values, where 0 and 1 represent the separation of voxels from the line (on side or the other), a registered LE image multiplied with the binary mask, a registered HE image multiplied with the binary mask, and the high energy tomographic volume data set 154 and the low-energy tomographic volume data set 152.

These additional datasets are also known as associated tomographic data sets, because they are associated with the creation of and manipulation upon the optimized combined tomographic volume data set 156. An operator uses these additional datasets in subsequent image analysis to, in one example, isolate one material from the optimized combined tomographic volume data set 156.

Figure 9:
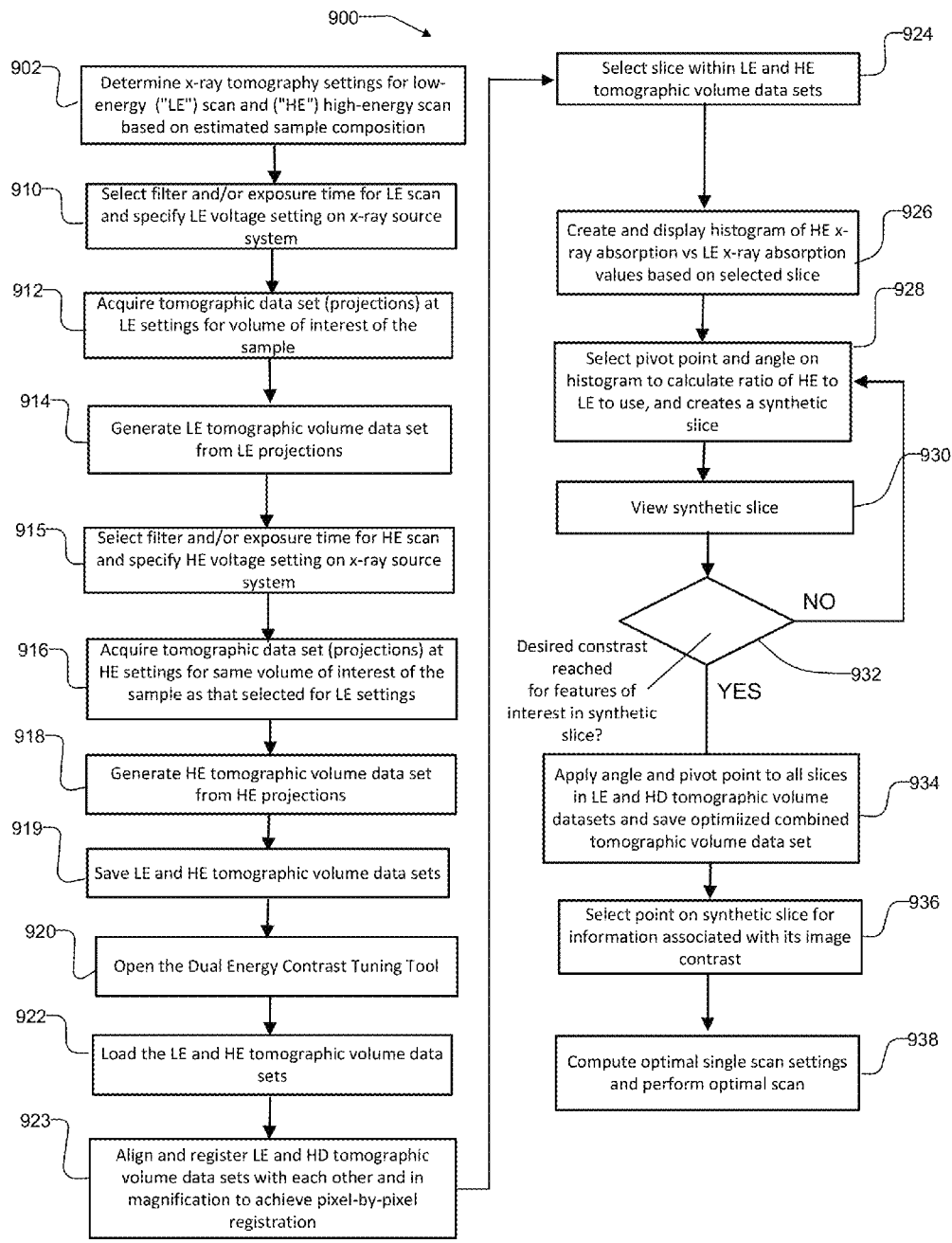
FIG. 9 is a flow diagram showing a method for data acquisition and image reconstruction for an x-ray imaging system according to principles of the present invention.

FIG. 9 is a flow diagram showing a method 900 for data acquisition and image reconstruction for an x-ray imaging system ("x-ray imaging system") according to principles of the present invention.

According to step 902, the operator determines the x-ray tomography settings for low-energy ("LE") scan and ("HE") high-energy scan based on estimated composition of the sample. In step 910, the operator selects a filter and/or exposure time for LE scan and specifies the LE voltage setting on x-ray source system. In step 912, the operator acquires a tomographic data set (projections) at LE settings for volume of interest of the sample. In step 914, the x-ray imaging system generates the LE tomographic volume data set from the LE projections.

In a similar fashion, the operator utilizes the x-ray imaging system to perform a high-energy scan of the same sample. In step 915, the operator selects a filter and/or exposure time for HE scan and specify HE voltage setting on the x-ray source system. In step 916, the x-ray imaging system acquires the tomographic data set (projections) at HE settings for same volume of interest of the sample as that selected for LE settings. In step 918, the x-ray imaging system generates the HE tomographic volume data set from the HE projections. In step 919, the operator saves the HE and LE tomographic volume data sets.

For the previous steps, the operator either performs the HE and LE scans separately, or uses the scout and scan application to perform the scans sequentially.

In step 920, the operator opens the dual energy contrast tuning tool, and in step 922 loads the LE and HE tomographic volume data sets. In step 923, the computer system aligns and registers the LE and HD tomographic volume data sets with each other and in magnification to achieve pixel-by-pixel registration.

In step 924, the operator selects a slice within the LE and HE tomographic volume data sets. In step 926, the computer system creates and displays a histogram of HE x-ray pixel intensity values vs LE x-ray pixel intensity values based on the selected slice.

In step 928, the operator selects a pivot point and angle on the histogram to calculate ratio of HE to LE to use, and create a synthetic slice. In step 930, the operator views the synthetic slice, and in step 932, if the desired image contrast has been achieved, the operator proceeds to step 934 to apply angle and pivot point to all slices in LE and HD tomographic volume datasets and saves the optimized combined tomographic volume data set 156. Otherwise, the operator repeats step 930 and step 932 until the desired image contrast has been achieved.

Once the desired image contrast has been achieved in step 934, the operator selects a point on the synthetic slice for information associated with its image contrast optimization, and computes optimal single-scan parameters and performs an optimal scan in step 938.

Figure 10A:
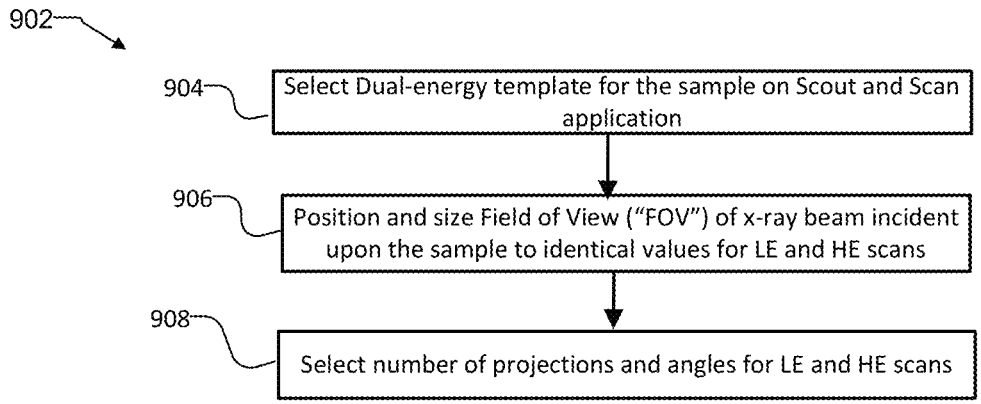
FIG. 10a is a flow diagram showing detail for steps within the flow chart of FIG. 9.

FIG. 10a is a flow diagram showing detail for step 902 within the flow chart of FIG. 9, for determining the x-ray tomography settings for low-energy ("LE") scan and ("HE") high-energy scan based on estimated sample composition. In step 904, the operator selects the appropriate dual-energy template associated with the sample on the Scout and Scan application. In step 906, the operator position and sizes the Field of View ("FOV") of the x-ray beam incident upon the sample to identical values for LE and HE scans. In step 908, the operator selects the number of projections and angles for LE and HE scans.

Figure 10B:
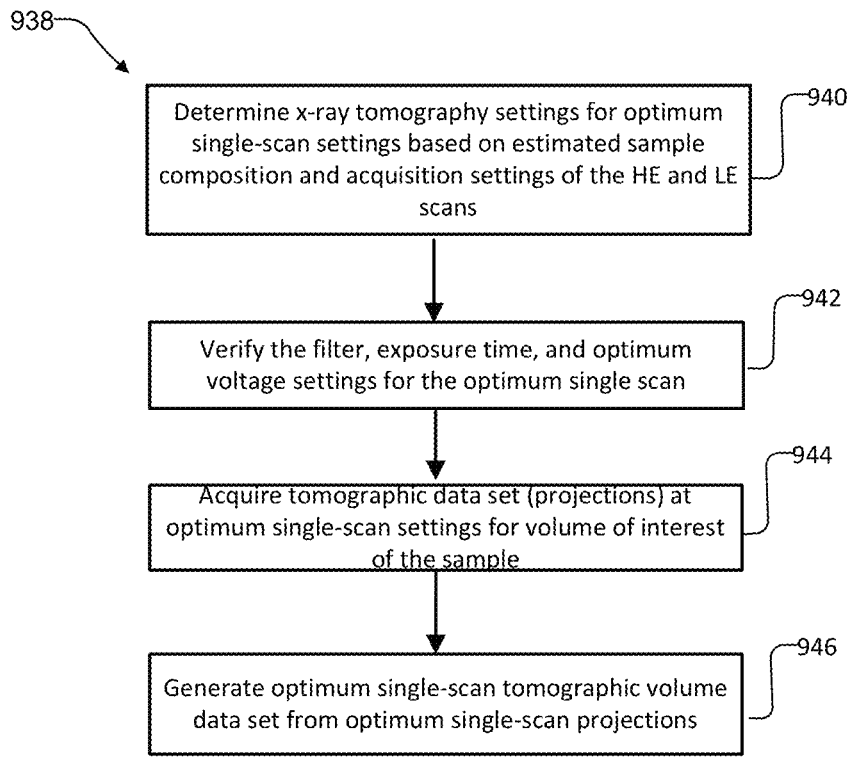
FIG. 10b is a flow diagram displaying a method for calculating optimum single scan parameters according to principles of the present invention.

FIG. 10b is a flow diagram showing detail for step 938 within the flow chart of FIG. 9, for calculating optimum single scan parameters according to principles of the present invention. In step 940, the computer system determines the x-ray tomography settings for optimum single-scan settings based on estimated sample composition and acquisition settings of the HE and LE scans. In step 942, the operator verifies the filter, exposure time, and optimum voltage settings for the optimum single scan. In step 944, the x-ray imaging system acquires the tomographic data set (projections) at optimum single-scan settings for the volume of interest of the sample. In step 946, x-ray imaging system generates an optimum single-scan tomographic volume data set from the optimum single-scan projections.

While this invention has been particularly shown and described with references to preferred embodiments thereof, it will be understood by those skilled in the art that various changes in form and details may be made therein without departing from the scope of the invention encompassed by the appended claims.

What is claimed is:

1. An x-ray imaging system, comprising:
   an x-ray source system for generating a high energy x-ray beam and a low energy x-ray beam;
   a sample holder for rotating a sample in the high energy x-ray beam and the low energy x-ray beam from the x-ray source system to perform a low-energy scan and a high-energy scan of the sample;
   a detector system for detecting the high energy x-ray beam and the low energy x-ray beam after transmission through the sample to generate projection data;
   a computer system generating a low-energy reconstructed tomographic volume data set from the low-energy scan and generating a high-energy reconstructed tomographic volume data set from the high-energy scan from the projection data, rendering simultaneous slice views from the low-energy and high-energy reconstructed tomographic volume data sets and presenting a mathematically combined synthetic slice, presenting an interactive graphic for displaying a two-dimensional slice selection from the low-energy and high-energy reconstructed tomographic volume data sets, rendering a low-energy slice view from the low-energy reconstructed tomographic volume data set and a high-energy slice view from the high-energy reconstructed tomographic volume data set for the same region of the sample, in response to user selection of a slice view within the two-dimensional slice selection graphic, creating a two-dimensional histogram of high-energy x-ray pixel intensity values versus low-energy x-ray pixel intensity values based on the selected slice in which intensity of points on the histogram is associated with a count of voxels with the low-energy and high-energy pixel intensity values respectively, and displaying the histogram.

2. The x-ray imaging system of claim 1, the computer system including user interface applications.

3. The x-ray imaging system of claim 2, wherein the user interface applications comprise:
   a dual energy contrast tuning tool; and
   a scout and scan application.

4. The x-ray imaging system of claim 1, wherein the low energy scan and the high energy scan are performed by irradiating a common volume of the sample.

5. The x-ray imaging system of claim 1, further comprises a filter changer mechanism that changes filters for filtering the x-ray beams received by the detector system.

6. The x-ray imaging system of claim 5, wherein the filter changer mechanism further comprises a fine adjustment control mechanism for a filter wheel.

7. The x-ray imaging system of claim 1, wherein the x-ray source system generates the low-energy x-ray beam using a low energy x-ray source and generates the high-energy x-ray beam using a high energy x-ray source.

8. The x-ray imaging system of claim 1, wherein the x-ray source system generates the low-energy x-ray beam using a low energy setting for an x-ray source and generates the high-energy x-ray beam using a high energy setting of the x-ray source.

9. The x-ray imaging system of claim 1, wherein the x-ray source system generates the low-energy x-ray beam using a low energy filter for an x-ray source and generates the high-energy x-ray beam using a high energy filter of the x-ray source.

10. The x-ray imaging system of claim 1, wherein the x-ray source system generates the low-energy x-ray beam using a low energy target for an x-ray source system and generates the high-energy x-ray beam using a high energy target of the x-ray source system.

11. The x-ray imaging system of claim 1, wherein the x-ray source system generates the low-energy x-ray beam using a low energy exposure time for an x-ray source and generates the high-energy x-ray beam using a high energy exposure of the x-ray source where the exposure times are optimized to account for different noise levels in the scans.

12. The x-ray imaging system of claim 1, wherein the computer system aligns and registers the low-energy and the high-energy reconstructed tomographic volume data sets with each other in three spatial dimensions.

13. The x-ray imaging system of claim 12, wherein the computer system aligns and registers the low-energy and the high-energy reconstructed tomographic volume data sets with each other in magnification.

14. The x-ray imaging system of claim 13, wherein the computer system scales the low-energy and the high-energy reconstructed tomographic volume data sets in intensity.

15. The x-ray imaging system of claim 1, wherein the histogram uses an offset logarithmic scale to assure that even single voxels display as recognizable points.

16. The x-ray imaging system of claim 1, wherein the computer system:
   creates synthetic slice for the selected slice through selection of pivot point and angle within the histogram, wherein the pivot point and angle specify the scaling and ratio of high-energy to low-energy pixel intensity values in the histogram;
   applies parameters used to generate the synthetic slice for the selected slice to the high-energy reconstructed tomographic volume data and the low-energy reconstructed tomographic volume data set to create an optimized combined tomographic volume data set; and
   saves the optimized combined tomographic volume data set.

17. The x-ray imaging system of claim 16, wherein the computer system computes optimum single scan acquisition settings based on the optimized combined tomographic volume data set.

18. The x-ray imaging system of claim 17, wherein the computer system:
   enables selection of a point on the optimized combined tomographic volume data set to obtain its associated scan settings; and
   utilizes the scan settings to perform an optimized scan of the sample or a new sample and generates a reconstructed tomographic volume data set for that sample.

19. The x-ray imaging system of claim 18, wherein the computer system saves the optimized combined tomographic volume data set and the associated scan settings from the point selection to a database.

20. An x-ray imaging system, comprising:
   an x-ray source system for generating a high energy x-ray beam and a low energy x-ray beam;
   a sample holder for rotating a sample in the high energy x-ray beam and the low energy x-ray beam from the x-ray source system to perform a low-energy scan and a high-energy scan of the sample;
   a detector system for detecting the high energy x-ray beam and the low energy x-ray beam after transmission through the sample to generate projection data;
   a computer system generating a low-energy reconstructed tomographic volume data set from the low-energy scan and generating a high-energy reconstructed tomographic volume data set from the high-energy scan from the projection data, rendering simultaneous slice views from the low-energy and high-energy reconstructed tomographic volume data sets and presenting a mathematically combined synthetic slice, identifying specific material constituents in the sample when there is a priori knowledge of basic sample constituents, enabling selection of a two-dimensional slice using an interactive graphic, creating a two-dimensional histogram of high-energy x-ray pixel intensity versus low-energy x-ray pixel intensity from the selected two-dimensional image slice, calculating the atomic molarity of elements within the sample from the histogram, and estimating microporosity of the sample by calculating the atomic molarity for an associated effective atomic number.

21. A dual energy contrast tuning tool executing on a computer system of an x-ray imaging system, comprising:
   a low-energy window for displaying low-energy slices from a low-energy reconstructed tomographic volume data set;
   a high-energy window for displaying high-energy slices from a high-energy reconstructed tomographic volume data set;
   a slice selection window having a two-dimensional slice selection interactive graphic for selecting slices from the sample; and
   a results window that displays synthetic slices that correspond to the slices selected in the slice selection window, the synthetic slices being generated by combining the low-energy reconstructed tomographic volume data set and the high-energy reconstructed tomographic volume data set.

22. A dual energy contrast tuning tool executing on a computer system of an x-ray imaging system, comprising:
   a low-energy window for displaying low-energy slices from a low-energy reconstructed tomographic volume data set;
   a high-energy window for displaying high-energy slices from a high-energy reconstructed tomographic volume data set;
   a slice selection window having a two-dimensional slice selection interactive graphic for selecting slices from the sample;
   a results window that displays synthetic slices generated by combining the low-energy reconstructed tomographic volume data set and the high-energy reconstructed tomographic volume data set; and
   a log window for displaying information associated with the dual energy contrast tuning tool operations.

23. A dual energy contrast tuning tool executing on a computer system of an x-ray imaging system, comprising:
- a low-energy window for displaying low-energy slices from a low-energy reconstructed tomographic volume data set;
- a high-energy window for displaying high-energy slices from a high-energy reconstructed tomographic volume data set;
- a slice selection window having a two-dimensional slice selection interactive graphic for selecting slices from the sample;
- a results window that displays synthetic slices generated by combining the low-energy reconstructed tomographic volume data set and the high-energy reconstructed tomographic volume data set; and
- a two-dimensional histogram tool showing pixel density as a function of low-energy and high-energy pixel intensity values and enabling selection of a pivot point and line slope parameters that are used to generate the synthetic slices from the low-energy reconstructed tomographic volume data set and the high-energy reconstructed tomographic volume data set.

24. The dual energy contrast tuning tool of claim 23, wherein the low-energy window displays the low-energy slice from the low-energy reconstructed tomographic volume data set, and the high-energy window displays the high-energy slice from the high-energy reconstructed tomographic volume data set, in response to user selection of a slice within the two-dimensional slice selection graphic.

25. The dual energy contrast tuning tool of claim 23, wherein the slice selection window further has:
- a slice selector slider bar and slice selector buttons for selecting the slice; and
- a slice number indicator that displays a slice number for the selected slice.

26. The dual energy contrast tuning tool of claim 23, wherein the histogram window includes:
- an angle selector slider bar for angle selection within the histogram;
- an angle indicator that displays the angle associated with the angle selection; and
- zoom in/out buttons for providing magnification of the histogram.

27. The dual energy contrast tuning tool of claim 23, wherein the histogram utilizes an offset logarithmic scale to assure that single pixels show up in the histogram as recognizable points.

28. The dual energy contrast tuning tool of claim 23, wherein the dual energy contrast tuning tool identifies specific material constituents in the sample when there is a priori knowledge of basic sample constituents.

29. The dual energy contrast tuning tool of claim 23, wherein information displayed by the dual-energy x-ray contrast tuning tool displays onto a display device connected to the computer system.

30. The dual energy contrast tuning tool of claim 23, wherein the location of points on the histogram associated with an irradiated point on the sample, represented as pixels, is a measure of how different the low-energy and high-energy x-ray pixel intensity values are for the irradiated point on the sample.

31. The dual energy contrast tuning tool of claim 30, wherein the computer system:
- creates the histogram of high-energy x-ray pixel intensity values versus low-energy x-ray pixel intensity values based on the selected slice in which intensity of points on the histogram associated with an irradiated point on the sample, represented as pixels, is a measure of how equal the low-energy and high-energy x-ray pixel intensity values are for the irradiated point on the sample; and
- displays the histogram.

32. The dual energy contrast tuning tool of claim 30, wherein the computer system:
- creates the synthetic slice for the selected slice through selection of pivot point and angle within the histogram, wherein the pivot point and angle specify the scale and ratio of high-energy to low-energy pixel intensity values in the histogram;
- applies parameters used to generate the synthetic slice for the selected slice to the high-energy reconstructed tomographic volume data and the low-energy reconstructed tomographic volume data set to create an optimized combined tomographic volume data set;
- displays the synthetic slice for the selected slice in the results window; and
- saves the optimized combined tomographic volume data set.

33. The dual energy contrast tuning tool of claim 32, wherein the computer system computes optimum single scan settings.

34. The dual energy contrast tuning tool of claim 33, wherein the computer system:
- enables selection of a point on the optimized combined tomographic volume data set to obtain its associated scan settings; and
- utilizes the scan settings to perform an optimized scan of the sample or a new sample and generates a reconstructed tomographic volume data set for that sample.

35. The dual energy contrast tuning tool of claim 34, wherein the dual energy contrast tuning tool includes a save button for saving the optimized combined tomographic volume data set and the associated scan settings from the point selection to the computer system.

36. A dual energy contrast tuning tool executing on a computer system of an x-ray imaging system, comprising:
- a low-energy window for displaying low-energy slices from a low-energy reconstructed tomographic volume data set;
- a high-energy window for displaying high-energy slices from a high-energy reconstructed tomographic volume data set;
- a slice selection window having a two-dimensional slice selection interactive graphic for selecting slices from the sample; and
- a results window that displays synthetic slices generated by combining the low-energy reconstructed tomographic volume data set and the high-energy reconstructed tomographic volume data set; and
- wherein:
  - the low-energy window includes a file browser button for selecting and displaying the filename associated with the low-energy reconstructed tomographic volume data set; and
  - the high-energy window includes a file browser button for selecting and displaying the filename associated with the high-energy reconstructed tomographic volume data set.

37. A dual energy contrast tuning tool executing on a computer system of an x-ray imaging system, comprising:
- a low-energy window for displaying low-energy slices from a low-energy reconstructed tomographic volume data set;

a high-energy window for displaying high-energy slices from a high-energy reconstructed tomographic volume data set;

a slice selection window having a two-dimensional slice selection interactive graphic for selecting slices from the sample; and a results window that displays synthetic slices generated by combining the low-energy reconstructed tomographic volume data set and the high-energy reconstructed tomographic volume data set;

wherein the dual energy contrast tuning tool: enables selection of a two-dimensional slice using an interactive graphic, creates a histogram of high-energy x-ray pixel intensity versus low-energy x-ray pixel intensity from the selected two-dimensional image slice, calculates the atomic molarity and effective atomic number of elements within the sample from the histogram, and estimates micro-porosity of the sample by calculating the atomic molarity for an associated effective atomic number.

38. A data acquisition and image reconstruction method for an x-ray imaging system, the method comprising:

loading a sample on a sample holder of the x-ray imaging system;

performing a low-energy scan by rotating the sample in a low energy x-ray beam from an x-ray source system of the x-ray imaging system;

performing a high-energy scan by rotating the sample in a high energy x-ray beam from the x-ray source system;

generating a low-energy reconstructed tomographic volume data set from the low-energy scan in a computer system;

generating a high-energy reconstructed tomographic volume data set from the high-energy scan in the computer system;

rendering slice views from the low-energy and high-energy reconstructed tomographic volume data sets on a display device of the computer system;

displaying an interactive graphic for two-dimensional slice selection;

in response to user selection of a slice within the two-dimensional slice selection graphic, displaying slice views from the low-energy reconstructed tomographic volume data set and the high-energy reconstructed tomographic volume data set for the same region of the sample;

creating a histogram of high-energy x-ray pixel intensity values versus low-energy x-ray pixel intensity values based on the selected slice in which intensity of points on the histogram associated with an irradiated point on the sample, represented as pixels, is a measure of how equal the low-energy and high-energy x-ray pixel intensity values are for the irradiated point on the sample;

displaying the histogram;

creating an optimized image for the selected slice through selection of pivot point and angle within the histogram, wherein the pivot point and angle specify a ratio of high-energy to low-energy pixel intensity values in the histogram;

applying parameters used to generate the optimized image for the selected slice to the high-energy reconstructed tomographic volume data and the low-energy reconstructed tomographic volume data set to create an optimized combined tomographic volume data set; and saving the optimized combined tomographic volume data set in the computer system.

39. The method of claim 38, wherein the x-ray source system generates the low-energy x-ray beam using a low energy x-ray source and generates the high-energy x-ray beam using a high energy x-ray source.

40. The method of claim 38, wherein the x-ray source system generates the low-energy x-ray beam using a low energy setting for an x-ray source and generates the high-energy x-ray beam using a high energy setting of the x-ray source.

41. The method of claim 38, wherein the x-ray source system generates the low-energy x-ray beam using a low energy filter for an x-ray source and generates the high-energy x-ray beam using a high energy filter of the x-ray source.

42. The method of claim 38, wherein the x-ray source system generates the low-energy x-ray beam using a low energy target for an x-ray source and generates the high-energy x-ray beam using a high energy target of the x-ray source.

43. The method of claim 38, wherein the x-ray source system generates the low-energy x-ray beam using a low energy exposure time for an x-ray source and generates the high-energy x-ray beam using a high energy exposure of the x-ray source.

44. The method of claim 38, wherein performing of the low energy scan and performing of the high energy scan includes irradiating a common volume of the sample.

45. The method of claim 38, further comprising aligning and registering the low-energy and the high-energy tomographic volume data sets with each other in three spatial dimensions.

46. The method of claim 45, further comprising aligning and registering the low-energy and the high-energy tomographic volume data sets with each other in magnification.

47. The method of claim 38, wherein displaying the histogram comprises utilizing an offset logarithmic scale in the histogram to assure that single pixels show up in the histogram as recognizable points.

48. The method in claim 38, further comprising computing optimum single scan settings.

49. The method in claim 48, wherein computing the optimum single scan settings comprises:

selecting a point on an optimized combined tomographic volume data set to obtain its associated scan settings; and using the scan settings to perform an optimized scan of the sample or a new sample and generating a reconstructed tomographic volume data set for that sample.

50. A data acquisition and image reconstruction method for an x-ray imaging system, the method comprising:

loading a sample on a sample holder of the x-ray imaging system;

performing a low-energy scan by rotating the sample in a low energy x-ray beam from an x-ray source system of the x-ray imaging system;

performing a high-energy scan by rotating the sample in a high energy x-ray beam from the x-ray source system;

generating a low-energy reconstructed tomographic volume data set from the low-energy scan in a computer system;

generating a high-energy reconstructed tomographic volume data set from the high-energy scan in the computer system; and rendering slice views from the low-energy and high-energy reconstructed tomographic volume data sets on a display device of the computer system;

identifying specific material constituents in the sample when there is a priori knowledge of basic sample constituents by selecting a two-dimensional slice using an interactive graphic and creating a histogram of high-energy x-ray pixel intensity versus low-energy x-ray pixel intensity from the selected two-dimensional image slice, and calculating the atomic molarity and effective atomic number of elements of elements within the sample from the histogram; and estimating micro-porosity from the specific material constituents in the sample.

51. A dual energy contrast tuning tool executing on a computer system of an x-ray imaging system, comprising:

a low-energy window for displaying low-energy slices from a low-energy reconstructed tomographic volume data set;

a high-energy window for displaying high-energy slices from a high-energy reconstructed tomographic volume data set;

a results window that displays synthetic slices generated by combining the low-energy reconstructed tomographic volume data set and the high-energy reconstructed tomographic volume data set;

a correlation tool that in response to an operator indicating a position in one of the windows, same positions are indicated in other windows; and a histogram window showing pixel density as a function of low-energy and high-energy pixel intensity values and enabling selection of a pivot point and line slope parameters that are used to generate the synthetic slices from the low-energy reconstructed tomographic volume data set and the high-energy reconstructed tomographic volume data set, wherein the correlation tool indicates a corresponding voxel in the histogram.

* * * * *